United States Patent
Nitto et al.

(10) Patent No.: US 8,748,572 B2
(45) Date of Patent: Jun. 10, 2014

(54) RNASE A PEPTIDES, FRAGMENTS AND USES THEREOF

(75) Inventors: Takeaki Nitto, Saga (JP); Kimberly D. Dyer, Reston, VA (US); Meggan Czapiga, Bethesda, MD (US); Helene F. Rosenberg, Bethesda, MD (US); Steven J. Siegel, Rockville, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 1417 days.

(21) Appl. No.: 12/438,700

(22) PCT Filed: Aug. 24, 2007

(86) PCT No.: PCT/US2007/018690
§ 371 (c)(1),
(2), (4) Date: Aug. 9, 2010

(87) PCT Pub. No.: WO2008/024457
PCT Pub. Date: Feb. 28, 2008

(65) Prior Publication Data
US 2010/0305025 A1    Dec. 2, 2010

Related U.S. Application Data

(60) Provisional application No. 60/840,268, filed on Aug. 24, 2006.

(51) Int. Cl.
C07K 7/06      (2006.01)
C07K 7/08      (2006.01)
C12Q 1/18      (2006.01)

(52) U.S. Cl.
USPC .............. 530/326; 530/328; 435/32

(58) Field of Classification Search
USPC ........................ 530/326, 328; 435/32
See application file for complete search history.

(56) References Cited

U.S. PATENT DOCUMENTS

2005/0113327 A1*   5/2005   Roiz et al. ............... 514/44

FOREIGN PATENT DOCUMENTS

WO       2005/051173        6/2005

OTHER PUBLICATIONS

Nitto et al., 2006, Evolution and Function of Leukocyte RNase a Ribonucleases of the Avian Species, Gallus gallus, Journal of Biological Chemistry, 281(35): 25622-25634.*
Klenova et al., 1992, Isolation of a cDNA clone encoding the RNase-Superfamily-Related Gene Highly Expressed in Chicken Bone Marrow Cells, Biochemical and Biophysical Research Communications, 185(1): 231-239.*
Nakano et al., 1992, Identification of genes differentially expressed in two types of v-myb-transformed avian myelomonocytic cells, Oncogene, 7: 527-534.*
Jeno et al., 1995, Internal Sequences from Proteins Digested in Polyacrylamide Gels, Analytical Biochemistry, 224: 75-82.*
Pai et al., Feb. 2006, Unique Peptide identification of RNase a Superfamily Sequences Based on Reinforced Merging Algorithms, Journal of Bioinformatics and Computational Biology, 4(1): 75-92.*
Nitto et al., The Journal of Biological Chemistry, 281(35):25622-25634 (2006).

* cited by examiner

*Primary Examiner* — Amber D Steele
(74) *Attorney, Agent, or Firm* — Edwards Wildman Palmer LLP; Peter F. Corless

(57) ABSTRACT

The present invention features isolated polypeptides that have bactericidal and angiogenic activities. The invention features isolated polypeptides comprising amino acid sequences of RNase A ribonucleases, fragments and variants thereof, pharmaceutical compositions, and methods for treatment of a subject.

4 Claims, 17 Drawing Sheets

FIG. 2A

```
RNase A-1   VPTYQDFLRT H VDFPKTSFPNIAAYNVMMVRRGINVHGR           40
RNase A-2   VPTYQDFLYK H MDFPKTSFPSNAAYNVMMVRRGMTAHGR           40
                      H11

K SLNTF VHTDPRNLNTLINQPNRALRTT QQQLPV TDCK         80
             K SFNTF VHTDPRNLNTLINQPDQALRTT RRHFRI TDCK         80
            K42                             ─────αA-1─────

LIRSHPTCSYTGNQFN H RVRVGC W GGLPV H LDGTFP          116
            LIRSHPTCRYSGNQFN R RVRVGC R GGLPV H LDGTSP          116
                             ─────αA-2─────    H110
```

Control

Leukocyte RNase A-1

Leukocyte RNase A-2

FIG. 6B

Mutations

Domain I  (A1 →A2): RTHV (9-12)→YKHM
Domain I  (A2 →A1): YKHM (9-12)→RTHV

Domain II (A1 →A2): QQQLPV (71-76) →RRHFRI
Domain II (A2 →A1): RRHFRI (71-76) →QQQLPV

Domain III (A1 →A2): $S^{89}$→R, $T^{91}$→S, $H^{97}$→R and $W^{104}$→R
Domain III (A2 →A1): $R^{89}$→S, $S^{91}$→T, $R^{97}$→H and $R^{104}$→W

H110A  $H^{110}$ →A

Domain II peptides
RNase A-1  NH2-TTQQLPVT-COOH
RNase A-2  NH2-TTRRHFRIT-COOH
Scrambled A-2  NH2-TRIRTRFHT-COOH Domain III peptides
RNase A-1  NH2-SYTGNQFNHRVRVGCWG-COOH
RNase A-2  NH2-RYSGNQFNRRVRVGCRG-COOH

FIG. 10A

```
Human angiogenin            AQDNSRYTHFLTQHYDAKPQGRD--DRYCESIMRRRGLTSP--CKDINTF
Mouse angionenin-1          --DDSRYTKFLTQHHDAKPKGRD--DRYCERMMKRRSLTSP--CKDVNTF
Chicken Leukocyte RNase A-1 -------QDFLRTHVDFPKTSFPNIAAYCNVMMVRRGINVHGRCKSLNTF
Chicken Leukocyte RNase A-2 -------QDFLYKHMDFPKTSFPSNAAYCNVMMVRRGMTAHGRCKSFNTF Human angiogenin            IHGNKRSIKAICENKNGNPHRENLRISKSSFQVTTCKLHGGSPWPPCQYR
Mouse angionenin-1          IHGNKSNIKAICG-ANGSPYRENLRMSKSPFQVTTCKHTGGSPRPPCQYR
Chicken Leukocyte RNase A-1 VHTDPRNLNTLCINQPNR-----ALRTTQQQLPVTDCKLIRSHP--TCSYT
Chicken Leukocyte RNase A-2 VHTDPRNLNTLCINQPDQ-----ALRTTRRHFRITDCKLIRSHP--TCRYS
                                                                  Domain III Human angiogenin            ATAGFRNVVVACENGLPVHLDQSIFRRP
Mouse angionenin-1          ASAGFRHVVIACENGLPVHFDESFFSL-
Chicken Leukocyte RNase A-1 GNQFNHRVRVGCWGGLPVHLDGTFP---
Chicken Leukocyte RNase A-2 GNQFNRRVRVGCRGGLPVHLDGTSP---
                            Domain IIII
```

Human (PDB: 1B1I)

Domain II
Domain III

Mouse (PDB: 2BWL)

Domain II
Domain III

SEQ ID NO: 1  gttccaacctac caagattttt tgcggacgca
cgtggacttcccgaagacatcgttcccaaacattgcagcttattgcaatg tcatgatggt
gagacgtggcataaatgtccatggaagatgcaaatccctcaacacctttgtgcataca
tcccagaaatctgaacactctctgcataaaccagcccaatcgggcccttcgtacaaca
gcagcaacttcctgtcacagactgtaagctgatcaggagccatccaacctgcagttac
cggcaatcaattcaaccatcgggtccgagtggggtgttggggagggcttcccgtgcat
ggatggcacc tttccatga SEQ ID NO: 2  VPTYQDFLRTHVDFPKTSFPNIAAYCNVMMVRRGINVHGR
CKSLNTFVHTDPRNLNTLCINQPNRALRTTQQQLPVTDCK
LIRSHPTCSYTGNQFNHRVRVGCWGGLPVHLDGTFP SEQ ID NO: 3  gttccaacctaccaaga tttttgtac aagcatatgg acttcccgaa gacatcgttc ccaagcaatg
cagcttattg caatgtcatg atggtgcggc gtggcatgac tgcccatgga agatgcaaat
ccttcaacac ctttgtgcat acagatccca gaaatctgaa cactctctgc ataaaccagc
ccgatcaggc ccttcgtaca acgcggcggc actttcgtat cacagactgt aagctgatca
ggagccatcc aacctgcaga tacagcggca atcaattcaa ccgccgggtc cgagtggggt
gtcggggagg cttcctgtg catctggatg cacctctcc atga SEQ ID NO: 4  VPTYQDFLYKHMDFPKTSFPSNAAYCNVMMVRRGMTAHGR
CKSFNTFVHTDPRNLNTLCINQPDQALRTTRRHFRITDCK
LIRSHPTCRYSGNQFNRRVRVGCRGGLPVHLDGTSP SEQ ID NO: 5  acaacgcggcggcactttcgtatcaca

SEQ ID NO: 6  TTRRHFRIT

SEQ ID NO: 7  agatacagcggcaatcaattcaaccgccgggtccgagtggggtgtcgggga

SEQ ID NO: 8  RYSGNQFNRRVRVGCRG

SEQ ID NO: 9  QPNRALRTTQQQLP

SEQ ID NO: 10  DQALRTTRRHFRIT

SEQ ID NO: 11  TRIRTRFHT

SEQ ID NO: 12  RYSGNQFNRRVRVGCRG

SEQ ID NO: 13  SYTGNQFNHRVRVGCWG

SEQ ID NO: 14  CKXXNTF

SEQ ID NO: 15  QQQLPV

SEQ ID NO: 16  RRHFRI

FIG. 12A

SEQ ID NO: 17  1 gtactaaataaaagtcacagctgatacccctgaaccattatcagaggaagagaacggttga
61 ggcaggacgaccctcaggagagacaggaaaagatcctcgcaaatacccaaagaga
121 ttttccttcctagacagcca tggccatgag ctccctgtgg tggactgcta tcctgctcct
181 agccctgacagtgtctatgtgctatggtgttccaacctac caagattttt tgcggacgca
241 cgtggacttcccgaagacatcgttcccaaacattgcagcttattgcaatg tcatgatggt
301 gagacgtggcataaatgtccatggaagatgcaaatccctcaacaccttttgtgcataca
361 tcccagaaatctgaacactctctgcataaaccagcccaatcgggcccttcgtacaaca
421 gcagcaacttcctgtcacagactgtaagctgatcaggagccatccaacctgcagttac
481 cggcaatcaattcaaccatcgggtccgagtgggggtgttggggagggcttcccgtgcat
541 ggatggcacc tttccatgac acttccccct tggaacatcc cttatccttt ttggagtccc
601 tgaccaatcctgaagctgtcctcactctgtcaactgcttttgggcttgga gaagaaggta
661 tcaaaacctctggcatcctg aatgctgctg cttaaccttg gttcccccta acgctttgat
721 aggctcctaagtcccactgg ctgtcccta ttgcctaagt ctcttctagc aacattgggt
781 tgacttcaac cctcctgaga tggttgcatt caggctcacc accactctct ttgctgcttt
841 tactcacataaacaaaagagaaataaaaacaagatttcttcatcaataatatttgcag
901 gaaattcttgttggaatggccattaaaaattaccctaaagtacccatgcaaaaaaaaa
961 aaaaaaaaaa aaaaaaa SEQ ID NO: 18  1 attatcagag gaagagaacg gttgaggcag gacgaccctc aggagagaca ggaaaagatc
61 ctcgcaaata cccaaagaga ggaaatttttc cttcctagac agccatggcc atgagctccc
121 tgtggtggac tgctatcctg ctcctagccc tgacagtgtc tatgtgctat ggtgttccaa
181 cctaccaaga ttttttgtac aagcatatgg acttcccgaa gacatcgttc ccaagcaatg
241 cagcttattg caatgtcatg atggtgcggc gtggcatgac tgcccatgga agatgcaaat
301 ccttcaacac ctttgtgcat acagatccca gaaatctgaa cactctctgc ataaaccagc
361 ccgatcaggc ccttcgtaca acgcggcggc acttcgtat cacagactgt aagctgatca
421 ggagccatcc aacctgcaga tacagcggca atcaattcaa ccgccgggtc cgagtggggt
481 gtcggggagg gcttcctgtg catctggatg gcacctctcc atgacacttc ccccttggaa
541 catcccttat ccttttttgga gtccctgacc aatcctgaag ctgtcctcac tctgtcaact
601 gcttttgggc ttggagaaga aggtatcaaa acctctggca tcctgtatgc tgctgcttaa
661 ccttggccca taccactctc tttgtagctt ttacttgcat agaacaaaac aaaaataata
721 aaaaagatt tcttcatcaa aaaaaaaaaa aaaaaaaaaa aaaaaa

SEQUENCE LISTING

```
<160> NUMBER OF SEQ ID NOS: 52

<210> SEQ ID NO 1
<211> LENGTH: 343
<212> TYPE: DNA
<213> ORGANISM: Gallus gallus

<400> SEQUENCE: 1
gttccaacct accaagattt tttgcggacg cacgtggact tcccgaagac atcgttccca      60
aacattgcag cttattgcaa tgtcatgatg gtgagacgtg gcataaatgt ccatggaaga     120
tgcaaatccc tcaacacctt tgtgcataca tcccagaaat ctgaacactc tctgcataaa     180
ccagcccaat cgggcccttc gtacaacagc agcaacttcc tgtcacagac tgtaagctga     240
tcaggagcca tccaacctgc agttaccggc aatcaattca accatcgggt ccgagtgggg     300
tgttggggag ggcttcccgt gcatggatgg cacctttcca tga                       343
```

```
<210> SEQ ID NO 2
<211> LENGTH: 116
<212> TYPE: PRT
<213> ORGANISM: Gallus gallus

<400> SEQUENCE: 2

Val Pro Thr Tyr Gln Asp Phe Leu Arg Thr His Val Asp Phe Pro Lys
 1               5                  10                  15

Thr Ser Phe Pro Asn Ile Ala Ala Tyr Cys Asn Val Met Met Val Arg
             20                  25                  30

Arg Gly Ile Asn Val His Gly Arg Cys Lys Ser Leu Asn Thr Phe Val
         35                  40                  45

His Thr Asp Pro Arg Asn Leu Asn Thr Leu Cys Ile Asn Gln Pro Asn
     50                  55                  60

Arg Ala Leu Arg Thr Thr Gln Gln Gln Leu Pro Val Thr Asp Cys Lys
 65                  70                  75                  80

Leu Ile Arg Ser His Pro Thr Cys Ser Tyr Thr Gly Asn Gln Phe Asn
                 85                  90                  95

His Arg Val Arg Val Gly Cys Trp Gly Gly Leu Pro Val His Leu Asp
                100                 105                 110

Gly Thr Phe Pro
            115

<210> SEQ ID NO 3
<211> LENGTH: 351
<212> TYPE: DNA
<213> ORGANISM: Gallus gallus

<400> SEQUENCE: 3
gttccaacct accaagattt tttgtacaag catatggact tcccgaagac atcgttccca      60
agcaatgcag cttattgcaa tgtcatgatg gtgcggcgtg gcatgactgc ccatggaaga     120
tgcaaatcct tcaacacctt tgtgcataca gatcccagaa atctgaacac tctctgcata     180
aaccagcccg atcaggccct tcgtacaacg cggcggcact ttcgtatcac agactgtaag     240
ctgatcagga gccatccaac ctgcagatac agcggcaatc aattcaaccg ccgggtccga     300
gtggggtgtc ggggagggct tcctgtgcat ctggatggca cctctccatg a              351

<210> SEQ ID NO 4
<211> LENGTH: 116
<212> TYPE: PRT
<213> ORGANISM: Gallus gallus

<400> SEQUENCE: 4

Val Pro Thr Tyr Gln Asp Phe Leu Tyr Lys His Met Asp Phe Pro Lys
 1               5                  10                  15

Thr Ser Phe Pro Ser Asn Ala Ala Tyr Cys Asn Val Met Met Val Arg
             20                  25                  30

Arg Gly Met Thr Ala His Gly Arg Cys Lys Ser Phe Asn Thr Phe Val
         35                  40                  45

His Thr Asp Pro Arg Asn Leu Asn Thr Leu Cys Ile Asn Gln Pro Asp
     50                  55                  60

Gln Ala Leu Arg Thr Thr Arg Arg His Phe Arg Ile Thr Asp Cys Lys
 65                  70                  75                  80

Leu Ile Arg Ser His Pro Thr Cys Arg Tyr Ser Gly Asn Gln Phe Asn
                 85                  90                  95

Arg Arg Val Arg Val Gly Cys Arg Gly Gly Leu Pro Val His Leu Asp
                100                 105                 110
```

Gly Thr Ser Pro
        115

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
acaacgcggc ggcactttcg tatcaca                                          27

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Thr Arg Arg His Phe Arg Ile Thr
1               5

<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
agatacagcg gcaatcaatt caaccgccgg gtccgagtgg ggtgtcgggg a               51

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Arg Tyr Ser Gly Asn Gln Phe Asn Arg Arg Val Arg Val Gly Cys Arg
1               5                   10                  15

Gly

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Pro Asn Arg Ala Leu Arg Thr Thr Gln Gln Gln Leu Pro
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic

```
            polypeptide

<400> SEQUENCE: 10

Asp Gln Ala Leu Arg Thr Thr Arg Arg His Phe Arg Ile Thr
 1               5                  10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Arg Ile Arg Thr Arg Phe His Thr
 1               5

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Arg Tyr Ser Gly Asn Gln Phe Asn Arg Arg Val Arg Val Gly Cys Arg
 1               5                  10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Tyr Thr Gly Asn Gln Phe Asn His Arg Val Arg Val Gly Cys Trp
 1               5                  10                  15

Gly

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: variable amino acid

<400> SEQUENCE: 14

Cys Lys Xaa Xaa Asn Thr Phe
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 15

Gln Gln Gln Leu Pro Val
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Arg His Phe Arg Ile
 1               5

<210> SEQ ID NO 17
<211> LENGTH: 961
<212> TYPE: DNA
<213> ORGANISM: Gallus gallus

<400> SEQUENCE: 17

| | | | | | |
|---|---|---|---|---|---|
| gtactaaata | aaagtcacag | ctgataccct | gaaccattat | cagaggaaga | gaacggttga | 60 |
| ggcaggacga | ccctcaggag | agacaggaaa | agatcctcgc | aaatacccaa | agagattttc | 120 |
| cttcctagac | agccatggcc | atgagctccc | tgtggtggac | tgctatcctg | ctcctagccc | 180 |
| tgacagtgtc | tatgtgctat | ggtgttccaa | cctaccaaga | ttttttgcgg | acgcacgtgg | 240 |
| acttcccgaa | gacatcgttc | ccaaacattg | cagcttattg | caatgtcatg | atggtgagac | 300 |
| gtggcataaa | tgtccatgga | agatgcaaat | ccctcaacac | cttttgtgcat | acatcccaga | 360 |
| aatctgaaca | ctctctgcat | aaaccagccc | aatcgggccc | ttcgtacaac | agcagcaact | 420 |
| tcctgtcaca | gactgtaagc | tgatcaggag | ccatccaacc | tgcagttacc | ggcaatcaat | 480 |
| tcaaccatcg | ggtccgagtg | gggtgttggg | gagggcttcc | cgtgcatgga | tggcaccttt | 540 |
| ccatgacact | tccccccttgg | aacatccctt | atccttttttg | gagtccctga | ccaatcctga | 600 |
| agctgtcctc | actctgtcaa | ctgcttttgg | gcttggagaa | gaaggtatca | aaacctctgg | 660 |
| catcctgaat | gctgctgctt | aaccttggtt | cccccctaacg | ctttgatagg | ctcctaagtc | 720 |
| ccactggctg | tcccttattg | cctaagtctc | ttctagcaac | attgggttga | cttcaaccct | 780 |
| cctgagatgg | ttgcattcag | gctcaccacc | actctctttg | ctgcttttac | tcacataaac | 840 |
| aaaaagagaa | ataaaaacaa | gatttcttca | tcaataatat | ttgcaggaaa | ttcttgttgg | 900 |
| aatggccatt | aaaaattacc | ctaaagtacc | catgcaaaaa | aaaaaaaaa | aaaaaaaaa | 960 |
| a | | | | | | 961 |

<210> SEQ ID NO 18
<211> LENGTH: 767
<212> TYPE: DNA
<213> ORGANISM: Gallus gallus

<400> SEQUENCE: 18

| | | | | | |
|---|---|---|---|---|---|
| attatcagag | gaagagaacg | gttgaggcag | gacgaccctc | aggagagaca | ggaaaagatc | 60 |
| ctcgcaaata | cccaaagaga | ggaaattttc | cttcctagac | agccatggcc | atgagctccc | 120 |
| tgtggtggac | tgctatcctg | ctcctagccc | tgacagtgtc | tatgtgctat | ggtgttccaa | 180 |
| cctaccaaga | ttttttgtac | aagcatatgg | acttcccgaa | gacatcgttc | ccaagcaatg | 240 |
| cagcttattg | caatgtcatg | atggtgcggc | gtggcatgac | tgcccatgga | agatgcaaat | 300 |
| ccttcaacac | ctttgtgcat | acagatccca | gaaatctgaa | cactctctgc | ataaaccagc | 360 |

```
ccgatcaggc ccttcgtaca acgcggcggc actttcgtat cacagactgt aagctgatca    420
ggagccatcc aacctgcaga tacagcggca atcaattcaa ccgccgggtc cgagtggggt    480
gtcggggagg gcttcctgtg catctggatg gcacctctcc atgacacttc cccctggaa    540 catcccttat cctttttgga gtccctgacc aatcctgaag ctgtcctcac tctgtcaact    600
gcttttgggc ttggagaaga aggtatcaaa acctctggca tcctgtatgc tgctgcttaa    660
ccttggccca taccactctc tttgtagctt ttacttgcat agaacaaaac aaaaataata    720 aaaaagatt tcttcatcaa aaaaaaaaaa aaaaaaaaaa aaaaaaa                   767
```

```
<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Thr His Val
  1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr Lys His Met
  1

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Gln Gln Leu Pro Val
  1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Arg His Phe Arg Ile
  1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 23

Thr Thr Gln Gln Gln Leu Pro Val Thr
1               5

<210> SEQ ID NO 24
<211> LENGTH: 124
<212> TYPE: PRT
<213> ORGANISM: Homo sapiens

<400> SEQUENCE: 24

Ala Gln Asp Asn Ser Arg Tyr Thr His Phe Leu Thr Gln His Tyr Asp
1               5                   10                  15

Ala Lys Pro Gln Gly Arg Asp Asp Arg Tyr Cys Glu Ser Ile Met Arg
            20                  25                  30

Arg Arg Gly Leu Thr Ser Pro Cys Lys Asp Ile Asn Thr Phe Ile His
        35                  40                  45

Gly Asn Lys Arg Ser Ile Lys Ala Ile Cys Glu Asn Lys Asn Gly Asn
    50                  55                  60

Pro His Arg Glu Asn Leu Arg Ile Ser Lys Ser Ser Phe Gln Val Thr
65                  70                  75                  80

Thr Cys Lys Leu His Gly Gly Ser Pro Trp Pro Pro Cys Gln Tyr Arg
                85                  90                  95

Ala Thr Ala Gly Phe Arg Asn Val Val Val Ala Cys Glu Asn Gly Leu
            100                 105                 110

Pro Val His Leu Asp Gln Ser Ile Phe Arg Arg Pro
        115                 120

<210> SEQ ID NO 25
<211> LENGTH: 120
<212> TYPE: PRT
<213> ORGANISM: Mus musculus

<400> SEQUENCE: 25

Asp Asp Ser Arg Tyr Thr Lys Phe Leu Thr Gln His His Asp Ala Lys
1               5                   10                  15

Pro Lys Gly Arg Asp Asp Arg Tyr Cys Glu Arg Met Met Lys Arg Arg
            20                  25                  30

Ser Leu Thr Ser Pro Cys Lys Asp Val Asn Thr Phe Ile His Gly Asn
        35                  40                  45

Lys Ser Asn Ile Lys Ala Ile Cys Gly Ala Asn Gly Ser Pro Tyr Arg
    50                  55                  60

Glu Asn Leu Arg Met Ser Lys Ser Pro Phe Gln Val Thr Thr Cys Lys
65                  70                  75                  80

His Thr Gly Gly Ser Pro Arg Pro Pro Cys Gln Tyr Arg Ala Ser Ala
                85                  90                  95

Gly Phe Arg His Val Val Ile Ala Cys Glu Asn Gly Leu Pro Val His
            100                 105                 110

Phe Asp Glu Ser Phe Phe Ser Leu
        115                 120

<210> SEQ ID NO 26
<211> LENGTH: 112
<212> TYPE: PRT
<213> ORGANISM: Gallus gallus

<400> SEQUENCE: 26

Gln Asp Phe Leu Arg Thr His Val Asp Phe Pro Lys Thr Ser Phe Pro
1               5                   10                  15

-continued

```
Asn Ile Ala Ala Tyr Cys Asn Val Met Met Val Arg Arg Gly Ile Asn
             20                  25                  30

Val His Gly Arg Cys Lys Ser Leu Asn Thr Phe Val His Thr Asp Pro
         35                  40                  45

Arg Asn Leu Asn Thr Leu Cys Ile Asn Gln Pro Asn Arg Ala Leu Arg
     50                  55                  60

Thr Thr Gln Gln Gln Leu Pro Val Thr Asp Cys Lys Leu Ile Arg Ser
 65                  70                  75                  80

His Pro Thr Cys Ser Tyr Thr Gly Asn Gln Phe Asn His Arg Val Arg
                 85                  90                  95

Val Gly Cys Trp Gly Gly Leu Pro Val His Leu Asp Gly Thr Phe Pro
            100                 105                 110
```

<210> SEQ ID NO 27
<211> LENGTH: 112
<212> TYPE: PRT
<213> ORGANISM: Gallus gallus

<400> SEQUENCE: 27

```
Gln Asp Phe Leu Tyr Lys His Met Asp Phe Pro Lys Thr Ser Phe Pro
 1               5                  10                  15

Ser Asn Ala Ala Tyr Cys Asn Val Met Met Val Arg Arg Gly Met Thr
             20                  25                  30

Ala His Gly Arg Cys Lys Ser Phe Asn Thr Phe Val His Thr Asp Pro
         35                  40                  45

Arg Asn Leu Asn Thr Leu Cys Ile Asn Gln Pro Asp Gln Ala Leu Arg
     50                  55                  60

Thr Thr Arg Arg His Phe Arg Ile Thr Asp Cys Lys Leu Ile Arg Ser
 65                  70                  75                  80

His Pro Thr Cys Arg Tyr Ser Gly Asn Gln Phe Asn Arg Arg Val Arg
                 85                  90                  95

Val Gly Cys Arg Gly Gly Leu Pro Val His Leu Asp Gly Thr Ser Pro
            100                 105                 110
```

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tggagaggtg ccatccagat gcacaggaag ccctccccg                               39

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tgaatgcaac catctcagga gggttgaagt                                         30

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
gttccaacct accaagattt tttg                                        24

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aagcttctgt tccaacctac caagattttt tg                               32

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gaattctgga aaggtgccat ccagatgcac                                  30

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aagcttctgt tccaacctac caagattttt tg                               32

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gaattctgga gaggtgccat ccagatgcac aggaagccct ccccg                 45

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
accaagattt tttgtacaag catatggact tcccgaagac                       40

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gtcttcggga agtccatatg cttgtacaaa aaatcttggt                    40

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
accaagattt tttgcggacg cacgtggact tcccgaagac                    40

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtcttcggga agtccacgtg cgtccgcaaa aaatcttggt                    40

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcccttcgta caacgcggcg gcactttcgt atcacagact gtaag             45

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cttacagtct gtgatacgaa agtgccgccg cgttgtacga agggc             45

<210> SEQ ID NO 41
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gcccttcgta caacgcagca gcaacttcct gtcacagact gtaag             45

<210> SEQ ID NO 42
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cttacagtct gtgacaggaa gttgctgctg cgttgtacga agggc       45

<210> SEQ ID NO 43
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aggagccatc caacctgcag atacagcggc aatcaattca a       41

<210> SEQ ID NO 44
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
caatcaattc aaccgccggg tccgagtggg gtgtcgggga gggcttcc       48

<210> SEQ ID NO 45
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ttgaattgat tgccgctgta tctgcaggtt ggatggctcc t       41

<210> SEQ ID NO 46
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggaagccctc cccgacaccc cactcggacc cggcggttga attgattg       48

<210> SEQ ID NO 47
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aggagccatc caacctgcag ttacaccggc aatcaattca a       41

<210> SEQ ID NO 48
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
caatcaattc aaccatcggg tccgagtggg gtgttgggga gggcttcc       48

```
<210> SEQ ID NO 49
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ttgaattgat tgccggtgta actgcaggtt ggatggctcc t                          41

<210> SEQ ID NO 50
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ggaagccctc cccaacaccc cactcggacc cgatggttga attgattg                   48

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ggagggcttc ccgtggctct ggatggcacc                                       30

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggtgccatcc agagccacgg gaagccctcc                                       30
```

RNASE A PEPTIDES, FRAGMENTS AND USES THEREOF

The present application claims status as a National Stage filing under 35 U.S.C. §371 of PCT/US2007/018690, which was filed Aug. 24, 2007 and claims the benefit of U.S. provisional application No. 60/840,268 filed Aug. 24, 2006, which is incorporated herein by reference in its entirety.

STATEMENT OF RIGHTS TO INVENTIONS MADE UNDER FEDERALLY SPONSORED RESEARCH

Research supporting this application was carried out by the United States of America as represented by the Secretary, Department of Health and Human Services.

BACKGROUND OF THE INVENTION

The RNase A ribonuclease gene family has been a source of information on unusual evolutionary constraints and their effects on protein structure and function at the molecular level. While RNase A ribonucleases maintain invariant disulfide bonds and catalytic components that are necessary for RNA degradation, there has been a large amount of divergence in other regions. As such, the specific patterns of diversification have been best understood among the RNase A ribonucleases of mammalian species. To date, divergence patterns among the non-mammalian RNase A ribonucleases have not been as clearly defined.

The RNase A ribonucleases have been implicated in a wide variety of physiologic functions, including angiogenesis, cellular apoptosis, and anti-tumor and anti-pathogen host defense via a complex array of seemingly unrelated molecular mechanisms; however still, the physiologic activities of many of the RNase A ribonucleases remain unexplored. This is also true of many of the mammalian RNase A ribonucleases. Some of the RNase A ribonucleases have been observed to promote angiogenesis. Angiogenic activity may be important in, for example, wound healing or tissue repair. Clinically, ulcers associated with diabetes or burn wounds that are caused by impaired blood supply, may be amenable to treatment with therapeutic angiogenic promoters. Thus, it would be desirable to promote angiogenesis in these conditions, and the activities of RNase A ribonucleases or peptide fragments could prove useful to that end.

The RNase A ribonucleases have been observed to be involved in anti-pathogen host defense. Antibiotics are a common therapy for the treatment or prevention of bacterial infection; however increasingly more bacteria are becoming resistant to conventional antibiotic therapy. Thus, a need in the art remains for new anti-bacterial agents. Accordingly, a greater understanding of the RNase A ribonuclease gene family, its functional domains, and its role in angiogenesis and anti-pathogen host defense may provide novel therapeutic agents.

SUMMARY OF THE INVENTION

In preferred aspects, the present invention features isolated polypeptides that have bactericidal and/or angiogenic activities. The invention also features isolated nucleic acid molecules and isolated polypeptides comprising amino acid sequences of RNaseA ribonucleases, fragments and variants thereof, pharmaceutical compositions, and methods for treatment of a subject. Other features and advantages of the invention will be apparent from the detailed description, and from the claims.

Accordingly, in one aspect the invention provides an isolated nucleic acid molecule selected from the group consisting of a nucleic acid molecule comprising a nucleotide sequence which is at least about 90% identical to the nucleotide sequence of SEQ ID NO: 1 or SEQ ID NO: 3, or a complement thereof, a nucleic acid molecule comprising a fragment of at least 15 nucleotides of a nucleic acid comprising the nucleotide sequence of SEQ ID NO: 1 or SEQ ID NO: 3, or a complement thereof, a nucleic acid molecule which encodes a polypeptide comprising an amino acid sequence at least about 90% identical to the amino acid sequence of SEQ ID NO: 2 or SEQ ID NO: 4, a nucleic acid molecule which encodes a fragment of a polypeptide comprising the amino acid sequence of SEQ ID NO: 2, or SEQ ID NO: 4; wherein the fragment comprises at least 5 contiguous amino acid residues of the amino acid sequence of SEQ ID NO: 2 or SEQ ID NO: 4, a nucleic acid molecule which encodes a variant of a polypeptide comprising the amino acid sequence of SEQ ID NO: 2 or SEQ ID NO: 4; wherein the nucleic acid molecule hybridizes to a complement of a nucleic acid molecule comprising SEQ ID NO: 1 or SEQ ID NO: 3, under stringent conditions, and the nucleic acid molecule of any of the above, which encodes a naturally occurring allelic variant.

In one embodiment, the isolated nucleic acid molecule is selected from the group consisting of a nucleic acid molecule comprising the nucleotide sequence of SEQ ID NO: 1 or SEQ ID NO: 3, or a complement thereof, and a nucleic acid molecule which encodes a polypeptide comprising the amino acid sequence of SEQ ID NO: 2 or SEQ ID NO: 4.

In another aspect, the invention provides an isolated polypeptide selected from the group consisting of a fragment of a polypeptide comprising the amino acid sequence of SEQ ID NO: 2 or SEQ ID NO: 4, wherein the fragment comprises at least 5 contiguous amino acids of SEQ ID NO: 2 or SEQ ID NO: 4, a variant of a polypeptide comprising the amino acid sequence of SEQ ID NO: 2 or SEQ ID NO: 4, wherein the polypeptide is encoded by a nucleic acid molecule which hybridizes to a complement of a nucleic acid molecule comprising SEQ ID NO: 1 or SEQ ID NO: 3, under stringent conditions, a naturally occurring allelic variant of a polypeptide comprising the amino acid sequence of SEQ ID NO: 2 or SEQ ID NO: 4, wherein the polypeptide is encoded by a nucleic acid molecule which hybridizes to a complement of a nucleic acid molecule comprising SEQ ID NO: 1 or SEQ ID NO: 3, under stringent conditions, a polypeptide which is encoded by a nucleic acid molecule comprising a nucleotide sequence which is at least about 90% identical to a nucleic acid comprising the nucleotide sequence of SEQ ID NO: 1 or SEQ ID NO: 3, and a polypeptide comprising an amino acid sequence which is at least about 30%, 40%, 50%, 60%, 70%, 80%, 90% or 95% homologous to the amino acid sequence of SEQ ID NO: 2 or SEQ ID NO: 4.

In one embodiment, the isolated polypeptide comprises the amino acid sequence of SEQ ID NO: 2 or SEQ ID NO: 4.

In a particular aspect, the invention provides an antibody that specifically binds *Gallus gallus* leukocyte RNase A-1 (SEQ ID NO: 9). In a further embodiment, the antibody is prepared using a peptide having the sequence QPNRALRT-TQQQLP (SEQ ID NO: 9).

In another particular aspect, the invention provides An antibody that specifically binds *Gallus gallus* leukocyte RNase A-2 (SEQ ID NO: 10). In a further embodiment, the antibody is prepared using a peptide having the sequence DQALRTTRRHFRIT (SEQ ID NO: 10).

In another aspect, the invention provides an isolated polypeptide comprising an amino acid fragment of SEQ ID NO: 2 or SEQ ID NO: 4. wherein the isolated polypeptide is bactericidal, bacteriostatic, or angiogenic. In one embodiment, the fragment is bactericidal. In another embodiment, the fragment is a bacteriostatic. In yet another embodiment, the fragment is angiogenic.

In one aspect, the invention provides an isolated polypeptide comprising the amino acid sequence TTRRHFRIT (SEQ ID NO: 6) wherein the peptide is bactericidal, bacteriostatic, or angiogenic.

In another aspect, the invention provides an isolated polypeptide comprising the amino acid sequence TRIRTRFHT (SEQ ID NO: 11) wherein the peptide is bactericidal, bacteriostatic, or angiogenic.

In another aspect, the invention provides an isolated polypeptide comprising the amino acids T,T,R,R,H,F,R,I,T (SEQ ID NO: 6) in any sequence, wherein the peptide is bactericidal, bacteriostatic, or angiogenic.

In still another aspect, the invention provides An isolated polypeptide comprising the amino acids T,R,I,R,T,R,F,H,T (SEQ ID NO: 11), in any sequence wherein the peptide is bactericidal, bacteriostatic, or angiogenic.

In a further aspect, the invention provides an isolated polypeptide comprising the amino acid sequence RYSGNQFNRRVRVGCRG (SEQ ID NO: 8) wherein the peptide is bactericidal, bacteriostatic, or angiogenic.

In another aspect, the invention provides an isolated polypeptide comprising the amino acids R,Y,S,G,N,Q,F,N,R,R,V,R,V,G,C,R,G (SEQ ID NO: 8) in any sequence, wherein the peptide is bactericidal, bacteriostatic, or angiogenic.

In one aspect, the invention provides an isolated polypeptide comprising an amino acid sequence of RNase A-2 (SEQ ID NO: 4), wherein said polypeptide is bactericidal.

In another aspect, the invention provides an isolated polypeptide comprising an amino acid sequence of RNase A-2 (SEQ ID NO: 4), wherein said polypeptide is bacteriostatic.

In a related aspect, the invention provides an isolated polypeptide comprising an amino acid sequence of RNase A-2 (SEQ ID NO: 4), wherein said polypeptide is angiogenic. In another related aspect, the invention provides an isolated polypeptide comprising chicken leukocyte RNase A-2 domain II, wherein said domain has the amino acid sequence set forth as SEQ ID NO: 6.

In another related aspect, the invention provides an isolated polypeptide comprising chicken leukocyte RNase A-2 domain III, wherein said domain has the amino acid sequence set forth as SEQ ID NO: 8.

In one embodiment the isolated polypeptide according to any of the aspects of the invention exhibits bactericidal activity. In a further embodiment the isolated polypeptide according to any of the aspects of the invention exhibits bacteriostatic activity. In another embodiment the isolated polypeptide according to any of the aspects of the invention exhibits angiogenic activity. In a further embodiment the isolated polypeptide according to any of the aspects of the invention exhibits ribonuclease activity. For example, in certain embodiments of the invention the RNase A-1 or RNase A-2, corresponding to SEQ ID NO: 1 or SEQ ID NO:3, respectively, have ribonuclease activity.

In one embodiment of the aspect, the bactericidal or bacteriostatic activity is against a gram negative or gram positive bacteria. In a related embodiment, the gram negative or gram positive bacteria is selected from the group consisting of: *Escherichia, Salmonella, Bacillus, Streptococcus*, and *Staphylococcus*. In a particular embodiment, the bactericidal or bacteriostatic activity is against *Escherichia coli*. In another particular embodiment, the bactericidal or bacteriostatic activity is against *Salmonella enterica*.

In another particular aspect, the invention provides a pharmaceutical composition comprising a polypeptide according to any one of the above aspects, and a pharmaceutically acceptable carrier.

In one embodiment, administration of the polypeptide induces at least about a 15% reduction in colony counts in a standard bacterial colony formation assay. IN another embodiment, administration of the polypeptide induces at least about a 25% reduction in colony counts in a standard bacterial colony formation assay. In a further embodiment, administration of the polypeptide induces at least about a 50% reduction in colony counts in a standard bacterial colony formation assay. In yet a further embodiment, administration of the polypeptide induces at least about a 90% reduction in colony counts in a standard bacterial colony formation assay.

In a further aspect of the invention is provided a method for treating a mammal having, or at risk of developing, a bacterial infection, comprising administering to the mammal a therapeutically effective amount of a polypeptide according to any one of the aspects of the invention.

In one embodiment, the method further comprises selecting a mammal that has a bacterial infection, or is at risk of developing a bacterial infection. In a particular embodiment, wherein bacterial infection is an *E. coli* infection. In another particular embodiment, the bacterial infection is a *Salmonella enterica* infection. In a further embodiment, the infection is selected from the group consisting of: infection of the skin, open wounds, burn wounds, and systemic infection.

In another embodiment of the method, the burn wound is infected with *Staphylococcus* or *Escherichia coli*. In still another embodiment, the *Staphylococcus* or *Escherichia coli* are antibiotic resistant. In another embodiment, the antibiotic is a beta-lactam antibiotic.

In a further aspect, the invention provides a method for treating a mammal having, or at risk of developing, a condition of impaired blood supply, comprising administering to the mammal therapeutically effective amount of a polypeptide according to any one of the aspects of the invention.

In one embodiment, the method further comprises selecting a mammal that has a condition of impaired blood supply, or is at risk of developing a condition of impaired blood supply. In another embodiment, the condition of impaired blood supply occurs in a skin ulceration or a wound.

In a particular embodiment of the method, administration of the polypeptide induces at least about a 5% increase in angiogenesis. In another embodiment, administration of the polypeptide induces at least about a 10% increase in angiogenesis. In a further embodiment, administration of the polypeptide induces at least about a 20% increase in angiogenesis. In still another particular embodiment, administration of the polypeptide induces at least about a 30%, 40% or 50% increase in angiogenesis. Such increases in angiogenesis as referred to herein may be determined by the chick aortic ring assay as exemplified in Example 3 below.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The terms "administration" or "administering" are defined to include an act of providing a compound or pharmaceutical composition of the invention to a subject in need of treatment.

The term "angiogenesis" is intended to refer to the process of the growth of new blood vessels. In certain embodiments, the term angiogenesis refers to the growth of new blood vessels from pre-existing blood vessels.

The phrase "condition of impaired blood supply" is meant to refer to a disease or condition wherein the amount of blood delivered to the target tissue, organ or area is less than the normal amount. A condition of impaired blood supply is characterized by vascular insufficiency in the tissue, organ or area of interest. A condition of impaired blood supply may, for example, occur in an ulcer or skin wound.

The terms "bactericidal" and "bactericidal activity" are intended to refer to the ability of an agent to kill a bacterium or a bacterial colony. An agent can be a compound or a molecule, including a peptide, a nucleotide, or a drug. An agent can be a cell or another organism.

The terms "bacteriostatic" and "bacteriostatic activity" are intended to refer to the ability of an agent to slow or inhibit the growth of a bacterium or a bacterial colony.

The term "reduction" means a negative alteration, or a decrease. Exemplary reductions according to the invention are reductions in bacterial colony counts, and include reductions of 15%, 25%, 50%, 75% or even 90%.

The terms "enzymatic activity" are meant to include the reactions catalyzed by the ribonuclease enzymes. As used herein, enzymatic activity includes ribonuclease activity.

By "fragment" is meant a portion (e.g., at least 5, 10, 25, 50, 100, 125, 150, 200, 250, 300, 350, 400, or 500 amino acids or nucleic acids) of a protein or nucleic acid molecule that is substantially identical to a reference protein or nucleic acid and retains the biological activity of the reference. In some embodiments the portion retains at least 50%, 75%, or 80%, or more preferably 90%, 95%, or even 99% of the biological activity of the reference protein or nucleic acid described herein, and retains at least one biological activity of the reference protein.

The term "Gram-negative bacterial cell" is intended to include the art-recognized definition of this term. Typically, Gram-negative bacteria can include *Gluconobacter, Rhizobium, Bradyrhizobium, Alcaligenes, Rhodobacter, Rhodococcus. Azospirillum, Rhodospirillum, Sphingomonas, Burkholderia, Desulfomonas, Geospirillum, Succinomonas, Aeromonas, Shewanella, Halochromatium, Citrobacter, Escherichia, Klebsiella, Zymomonas, Zymobacter*, and *Acetobacter*.

The term "Gram-positive bacteria" is intended to include the art-recognized definition of this term. Typically, Gram-positive bacteria can include *Fibrobacter, Acidobacter, Bacteroides, Sphingobacterium, Actinomyces, Corynebacterium, Nocardia, Rhodococcus, Propionibacterium, Bifidobacterium, Bacillus, Geobacillus, Paenibacillus, Sulfobacillus, Clostridium, Anaerobacter, Eubacterium, Streptococcus, Lactobacillus, Leuconostoc, Enterococcus, Lactococcus, Thermobifida, Cellulomonas*, and *Sarcina*.

The term "homologue", as used herein, refers to a protein or nucleic acid sharing a certain degree of sequence "identity" or sequence "similarity" with a given protein, or the nucleic acid encoding the given protein. The term "percent identity" refers to the percentage of residues in two sequences that are the same when aligned for maximum correspondence. Sequence "similarity" is related to sequence "identity", but differs in that residues that are not exactly the same as each other, but that are functionally "similar" are taken into consideration.

The term "hybridizes under stringent conditions" is intended to describe conditions for hybridization and washing under which nucleotide sequences at least 60%, 70%, 75%, 80%, 85%, 90%, or 95% homologous to each other typically remain hybridized to each other. Hybridization conditions are known to those skilled in the art and can be found in Current Protocols in Molecular Biology, John Wiley & Sons, N.Y., 1991. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are defined as equivalent to hybridization in 6× sodium chloride/sodium citrate (SSC) at 45° C., followed by a wash in 0.2×SSC, 0.1% SDS at 65° C.

The term "identical" is intended to include a first amino acid or nucleotide sequence which contains a sufficient or minimum number of the same or equivalent amino acid residues or nucleotides, e.g., an amino acid residue which has a similar side chain, to a second amino acid or nucleotide sequence such that the first and second amino acid or nucleotide sequences share common structural domains and/or a common functional activity. Accordingly, a homologous or identical nucleic acid molecule of the invention is at least 15, 20, 25, 30 or more nucleotides in length and hybridizes under stringent conditions to a nucleic acid molecule encoding the amino acid sequence of SEQ ID NO: 2 or to a nucleic acid molecule encoding the amino acid sequence of SEQ ID NO: 4. Preferably, the molecule hybridizes under highly stringent conditions. In other embodiments, the nucleic acid is at least 15-20 nucleotides in length.

The term "increase" means a positive alteration. Exemplary increases include 10%, 20%, 30%, 40% or even 50%.

The terms "isolated," "purified," or "biologically pure" refer to material that is free to varying degrees from components which normally accompany it as found in its native state. Various levels of purity may be applied as needed according to this invention in the different methodologies set forth herein; the customary purity standards known in the art may be used if no standard is otherwise specified.

By "isolated nucleic acid molecule" is meant a nucleic acid (e.g., a DNA, RNA, or analog thereof) that is free of the genes which, in the naturally occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule which is transcribed from a DNA molecule, as well as a recombinant DNA which is part of a hybrid gene encoding additional polypeptide sequence.

The term an "isolated polypeptide" (e.g., an isolated or purified biosynthetic enzyme) is substantially free of cellular material or other contaminating polypeptides from the microorganism from which the polypeptide is derived, or substantially free from chemical precursors or other chemicals when chemically synthesized.

The phrase "mutant nucleic acid molecule" or "mutant gene" is intended to include a nucleic acid molecule or gene having a nucleotide sequence which includes at least one alteration (e.g., substitution, insertion, deletion) such that the polypeptide or polypeptide that can be encoded by said mutant exhibits an activity that differs from the polypeptide or polypeptide encoded by the wild-type nucleic acid molecule or gene.

By "polypeptide" is meant any chain of amino acids, or analogs thereof, regardless of length or post-translational modification. The terms "polypeptide" and "peptide" are meant to be used interchangeably.

The terms "RNase A" and "RNase A ribonuclease" refer to the RNase A ribonuclease gene family. Generally, RNases are involved in RNA degradation. Members of the RNase A ribonuclease gene family are present in non-mammalian and mammalian species. RNase A ribonucleases are found in all vertebrates, but not in invertebrates. In specific embodiments of the present invention, the RNase A ribonucleases are from the chicken, *Gallus gallus*. In exemplary embodiments the RNase A Ribonucleases are *Gallus gallus* RNase A-1 and *Gallus gallus* RNase A-2.

The term "RNase A activity" is meant to include an activity of an isolated RNase A polypeptide or fragment that is one or more of bactericidal, bacteriostatic, angiogenic or ribonucleolytic.

By "substantially identical" is meant a protein or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 90%, and most preferably 91%, 92%, 93%, 94%, 95%, 96%, 97%, 98%, 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

The term "subject" refers to animals, typically mammalian animals, such as primates (humans, apes, gibbons, chimpanzees, orangutans, macaques), domestic animals (dogs and cats), farm animals (horses, cattle, goats, sheep, pigs) and experimental animals (mouse, rat, rabbit, guinea pig). Subjects include animal disease models (e.g., tumor bearing mice).

The terms "therapeutically effective amount" used herein refer to an amount sufficient to produce the desired affect. Effective amounts therefore include one or more of: killing a bacterium or a bacterial colony, slowing or inhibiting the growth of a bacterium or a bacterial colony, or promoting the growth of new blood vessels.

The term "treating" is meant to refer to killing a bacterium or a bacterial colony, slowing or inhibiting the growth of a bacterium or a bacterial colony, or promoting the growth of new blood vessels.

Other aspects of the invention are disclosed infra.

BRIEF DESCRIPTION OF THE DRAWINGS

In FIG. 3, chicken aortic rings were incubated with 2 μM of recombinant chicken leukocyte RNase A-1 (B) or A-2 (C). A sham protein isolate prepared with the same procedure with vector transfectant only was used as control (A). Photographs were taken at t=24 h of incubation. See Table 2 for quantitative analysis.

FIGS. 12A & B list SEQ ID Nos 1-18 and the corresponding sequences. SEQ ID NO: 1 and SEQ ID NO: 3 correspond to the processed nucleotide sequences of *Gallus gallus* leukocyte ribonuclease A-1 and A-2, respectively. SEQ ID NO: 2 and SEQ ID NO: 4 indicate the corresponding translated sequences of *Gallus gallus* leukocyte ribonuclease A-1 and A-2, respectively. SEQ ID Nos 5 and 6 correspond to RNase A-2 Domain II nucleotide and polypeptide sequences (SEQ ID NOs: 5 and 6, respectively), A-2 Domain III nucleotide and polypeptide sequences (SEQ ID NOs: 7 and 8, respectively). SEQ ID Nos: 9 and 10 correspond to the antibody used to detect *Gallus gallus* leukocyte RNase A-1 (SEQ ID NO: 9), and the antibody used to detect *Gallus gallus* leukocyte RNase A-2 (SEQ ID NO: 10). SEQ ID NO: 11 corresponds to the polypeptide sequence TRIRTRFHT. SEQ ID NO: 13 corresponds to RNaseA-1 Domain III polypeptide sequence SYTGNQFNHRVRVGCWG (SEQ ID NO: 13). SEQ ID NOs: 14-16 correspond to amino acid sequences of RNase A polypeptides. SEQ ID NO: 17 corresponds to full length chicken leukocyte RNase A-1, and SEQ ID NO: 18 corresponds to full length chicken leukocyte RNase A-2.

DETAILED DESCRIPTION OF THE INVENTION

Figure 1:
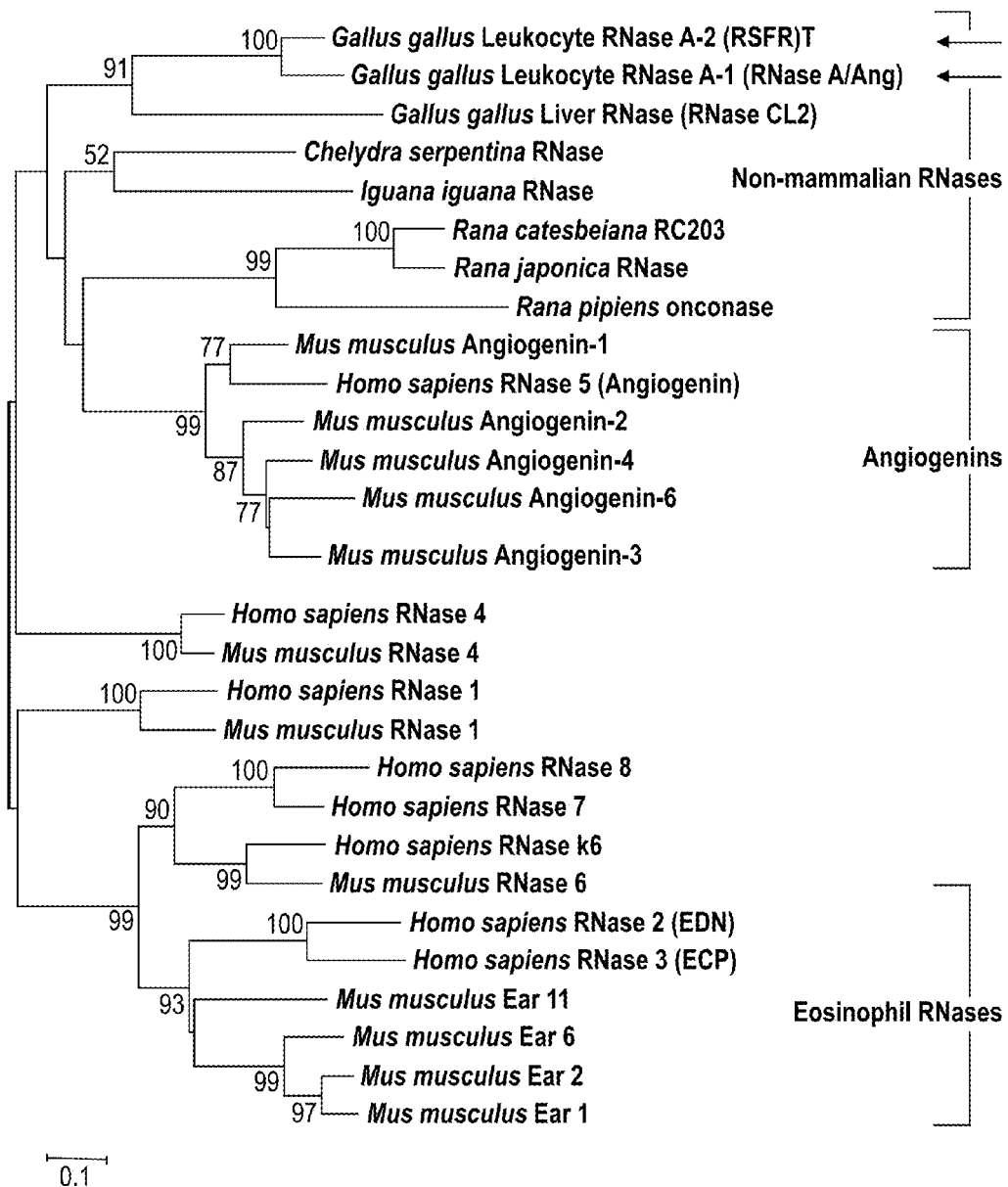
FIG. 1 is a diagram of a phylogenetic tree. The neighbor-joining phylogenetic tree documents relationships among the major RNase A ribonuclease lineages. Arrows indicate the relative positions of the two chicken leukocyte ribonucleases, renamed RNase A-1 and RNase A-2, together with the other non-mammalian RNase A ribonucleases, which as a group are most closely related to the mammalian angiogenin/RNase 5 lineage [11]. Amino acid sequences were aligned using ClustalW software and an unrooted neighbor-joining phylogenetic tree (no. of differences, complete deletion of gaps) was created with MEGA 2.1 [33]. Only bootstrap values (1000 replicates) over 50 are shown. Sequences shown are from GenBank and NCBI sequence databases; accession numbers are listed in the Methods section.

In preferred aspects, the present invention features isolated polypeptides that have bactericidal, bacteriostatic, and/or angiogenic activities. The invention features isolated polypeptides comprising amino acid sequences of RNase A ribonucleases, fragments and variants thereof, pharmaceutical compositions, and methods for treatment of a subject.

RNase A Ribonuclease Gene Family

RNase A ribonucleases have been implicated in a wide variety of physiologic functions, and have been observed to promote angiogenesis, cellular apoptosis, anti-tumor and anti-pathogen host defense via a complex array of seemingly unrelated molecular mechanisms [1-8]. The specific patterns of diversification are best understood among the RNase A ribonucleases of mammalian species. Four major RNase A lineages have been described in mammals [6]: the pancreatic RNases, or RNases 1, which include the prototype, bovine pancreatic RNase A; a second group including the eosinophil ribonucleases EDN(RNases 2), ECP (RNases 3) and RNases 6, 7 and 8; a third group that includes the RNases 4; and a final group that includes the angiogenins (RNases 5). There are also several genes, such as RNases 9-13 in the human genome, that are distantly related to the RNase A family based on amino acid sequence homology, but that are missing of one or more elements necessary for enzymatic activity [9-13]. Not all RNase A lineages are found in every mammalian species, and there are some recently described mammalian RNase A ribonucleases that cannot be clearly assigned to a specific lineage or group [14].

In contrast, the non-mammalian RNase A ribonucleases have not been as clearly defined. Several RNase A ribonucleases of the frog genus *Rana* have been isolated [15-18], including the cancer biotherapeutic agent, onconase [19]. Also characterized are several RNase A ribonucleases from birds [14, 20-22] and reptiles [23-25]. However, with only a small number of sequences characterized, there is not an adequate sense of the specific interrelationships or unique lineages of the non-mammalian RNase A ribonucleases. Chicken RNase A/angigogenin, named for structural similarity, as opposed to functional analysis, was identified by Nakano and Graf (NCBI database Accession No. CAA43495) [20] from RNA from v-myb transformed myeloblasts. Ribonuclease superfamily-related (RSFR) was cloned by Lobanenkov and colleagues (NCBI database Accession No. CAA46006) [21] from chicken bone marrow as part of an unrelated subtractive hybridization study. Cho and colleagues [11] performed an exhaustive search of the recently published chicken genome, and have concluded that there are only three RNase A ribonucleases, the two leukocyte-associated RNases on chromosome 6, and a more distantly-related sequence on chromosome 4.

Featured in the present invention are RNase A ribonucleases (e.g. RNase A-1 and RNase A-2 polypeptides) that are, for example, bactericidal, bacteriostatic, ribonucleolytic and/or angiogenic.

Isolated Nucleic Acids

Included in the scope of the present invention are isolated nucleic acid molecules. The nucleic acid molecule can be single-stranded or double-stranded DNA. The isolated nucleic acid molecule of the invention can include a nucleic acid molecule which is free of sequences which naturally flank the nucleic acid molecule (i.e., sequences located at the 5' and 3' ends of the nucleic acid molecule) in the chromosomal DNA of the organism from which the nucleic acid is derived. For instance, an isolated nucleic acid molecule can contain less than about 10 kb, 5 kb, 4 kb, 3 kb, 2 kb, 1 kb, 0.5 kb, 0.1 kb, 50 bp, 25 bp or 10 bp of nucleotide sequences which naturally flank the nucleic acid molecule in chromosomal DNA of the microorganism from which the nucleic acid molecule is derived. Moreover, an "isolated" nucleic acid molecule, such as a cDNA molecule, can be substantially free of other cellular materials when produced by recombinant techniques, or substantially free of chemical precursors or other chemicals when chemically synthesized.

In embodiments of the invention, the nucleic acid corresponds to the mature form of chicken leukocyte RNase A-1 (SEQ ID NO: 1):

```
gttccaacctac caagattttt tgcggacgca cgtggacttcccga agacatcgttcccaaacattgcagcttattgcaatg tcatgatggtg gagacgtggcataaatgtccatggaagatgcaaatccctcaacaccttt tgtgcatacatcccagaaatctgaacactctctgcataaaccagccca atcgggcccttcgtacaacagcagcaacttcctgtcacagactgtaag ctgatcaggagccatccaacctgcagttaccggcaatcaattcaacca tcgggtccgagtggggtgttggggagggcttcccgtgcatggatggca cc tttccatga
```

The full length chicken leukocyte RNase A-1 (SEQ ID NO: 17), as shown below, was previously deposited as GenBank Accession No. DQ395275, and includes the signal sequence.

```
  1 gtactaaataaaagtcacagctgatacctgaaccattatcagaggaagagaacggttga 61 ggcaggacgaccctcaggagagacaggaaaagatcctcgcaaatacccaaagaga 121 ttttccttcctagacagcca tggccatgag ctccctgtgg tggactgcta tcctgctcct 181 agccctgacagtgtctatgtgctatggtgttccaacctac caagattttt tgcggacgca 241 cgtggacttcccgaagacatcgttcccaaacattgcagcttattgcaatg tcatgatggt 301 gagacgtggcataaatgtccatggaagatgcaaatccctcaacacctttgtgcataca 361 tcccagaaatctgaacactctctgcataaaccagcccaatcgggcccttcgtacaaca 421 gcagcaacttectgtcacagactgtaagctgatcaggagccatccaacctgcagttac 481 cggcaatcaattcaaccatcgggtccgagtggggtgttggggagggcttcccgtgcat 541 ggatggcacc tttccatgac acttccccct tggaacatcc cttatccttt ttggagtccc 601 tgaccaatcctgaagctgtcctcactctgtcaactgcttttgggcttgga gaagaaggta 661 tcaaaadctctggcatcctg aatgctgctg cttaaccttg gttcccccta acgctttgat 721 aggctcctaagtccactgg ctgtcccta ttgcctaagt ctcttctagc aacattgggt 781 tgacttcaac cctcctgaga tggttgcatt caggctcacc accactctct ttgctgcttt 841 tactcacataaacaaaaagagaaataaaaacaagatttcttcatcaataatatttgcag 901 gaaattcttgttggaatggccattaaaaattaccctaaagtacccatgcaaaaaaaaa 961 aaaaaaaaaa aaaaaaa
```

In other embodiments of the invention, the nucleic acid corresponds to the mature form of chicken leukocyte RNase A-2 (SEQ ID NO: 3):

```
gttccaacctaccaaga tttttgtac aagcatatgg acttcccgaa gacatcgttc ccaagcaatg cagcttattg caatgtcatg atggtcggc gtggcatgac tgcccatgga agatgcaaat ccttcaacac ctttgtgcat acagatccca gaaatctgaa
```

-continued
```
cactctctgc ataaaccagc ccgatcaggc ccttcgtaca acgcggcggc actttcgtat cacagactgt aagctgatca ggagccatcc aacctgcaga tacagcggca atcaattcaa ccgccgggtc cgagtggggt gtcggggagg gcttcctgtg catctggatg gcacctctcc atga
```

The full length chicken leukocyte RNase A-2 (SEQ ID NO: 18), as shown below, was previously deposited as GenBank Accession No. DQ395276, and includes the signal sequence.

```
  1 attatcagag gaagagaacg gttgaggcag gacgaccctc aggagagaca ggaaaagatc 61 ctcgcaaata cccaaagaga ggaaattttc cttcctagac agccatggcc atgagctccc 121 tgtggtggac tgctatcctg ctcctagccc tgacagtgtc tatgtgctat ggtgttccaa 181 cctaccaaga ttttttgtac aagcatatgg acttcccgaa gacatcgttc ccaagcaatg 241 cagcttattg caatgtcatg atggtgcggc gtggcatgac tgcccatgga agatgcaaat 301 ccttcaacac ctttgtgcat acagatccca gaaatctgaa cactctctgc ataaaccagc 361 ccgatcaggc ccttcgtaca acgcggcggc actttcgtat cacagactgt aagctgatca 421 ggagccatcc aacctgcaga tacagcggca atcaattcaa ccgccgggtc cgagtggggt 481 gtcggggagg gcttcctgtg catctggatg gcacctctcc atgacacttc ccccttggaa 541 catcccttat cctttttgga gtccctgacc aatcctgaag ctgtcctcac tctgtcaact 601 gcttttgggc ttggagaaga aggtatcaaa acctctggca tcctgtatgc tgctgcttaa 661 ccttggccca taccactctc tttgtagctt ttacttgcat agaacaaaac aaaaataata 721 aaaaagatt tcttcatcaa aaaaaaaaaa aaaaaaaaa aaaaaaa
```

In one embodiment, an isolated nucleic acid molecule of the invention comprises a nucleotide sequence which is at least about 90% identical, and most preferably 91%, 92%, 93%, 94%, 95%, 96%, 97%, 98%, 99% identical to the nucleotide sequence of SEQ ID NO: 1 or SEQ ID NO: 3, or a complement thereof. In another embodiment, the nucleic acid molecule of the invention comprises a fragment of at least about 5-25, more preferably 10-15 nucleotides of a nucleic acid comprising the nucleotide sequence of SEQ ID NO: 1 or SEQ ID NO: 3, or a complement thereof, that retains the biological activity of SEQ ID NO: 1 or SEQ ID NO: 3, e.g. the fragments are, for example, bactericidal, bacteriostatic, ribonucleolytic and/or angiogenic. In yet another embodiment, an isolated nucleic acid molecule of the invention encodes a nucleic acid molecule which encodes a polypeptide comprising an amino acid sequence that is at least about 50% homologous to the amino acid sequence of SEQ ID NO: 2 or SEQ ID NO:4, and retains the biological activity of SEQ ID NO: 2 or SEQ ID NO: 4, e.g. retains, for example, bactericidal, bacteriostatic, ribonucleolytic or angiogenic activity.

Typically, the terms "sequence identity" or "homologue" include a nucleotide or polypeptide sharing at least about 30-35%, advantageously at least about 35-40%, more advantageously at least about 40-50%, and even more advantageously at least about 60%, 70%, 80%, 90% or more identity with the amino acid sequence of a wild-type polypeptide or polypeptide described herein and having a substantially equivalent functional or biological activity as the wild-type RNase A polypeptide or polypeptide. For example, a RNase A homologue shares at least about 30-35%, advantageously at least about 35-40%, more advantageously at least about 40-50%, and even more advantageously at least about 90%, 91%, 92%, 93%, 94%, 95%, 96%, 97%, 98%, 99% identity with the polypeptide having the amino acid sequence set forth as SEQ ID NO: 2 or SEQ ID NO: 4, and has substantially equivalent functional or biological activities (i.e., is a functional equivalent) of the polypeptide having the amino acid sequence set forth as SEQ ID NO: 2 or SEQ ID NO: 4 (e.g., has a substantially equivalent RNase A-1 or RNase A-2 activities).

In another embodiment, an isolated nucleic acid molecule encodes a variant of a polypeptide comprising the amino acid sequence of SEQ ID NO: 2 or SEQ ID NO: 4, wherein the nucleic acid molecule hybridizes to a complement of a nucleic acid molecule comprising SEQ ID NO: 1 or SEQ ID NO: 3, under stringent conditions. Such stringent conditions are known to those skilled in the art and can be found in *Current Protocols in Molecular Biology*, John Wiley & Sons, N.Y. (1989), 6.3.1-6.3.6. A particular, non-limiting example of stringent (e.g. high stringency) hybridization conditions are hybridization in 6× sodium chloride/sodium citrate (SSC) at about 45° C., followed by one or more washes in 0.2×SSC, 0.1% SDS at 50-65° C. Advantageously, an isolated nucleic acid molecule of the invention that hybridizes under stringent conditions to the sequence of SEQ ID NO: 1 or SEQ ID NO: 3 corresponding to a naturally-occurring nucleic acid molecule or a naturally occurring allelic variant. Typically, a naturally-occurring nucleic acid molecule includes an RNA or DNA molecule having a nucleotide sequence that occurs in nature.

A nucleic acid molecule of the present invention (e.g., a nucleic acid molecule having the nucleotide sequence of SEQ ID NO: 1, SEQ ID NO:3, SEQ ID NO:3 or SEQ ID NO:7 can be isolated using standard molecular biology techniques and the sequence information provided herein. For example, nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989) or can be isolated by the polymerase chain reaction using synthetic oligonucleotide primers designed based upon the sequence of SEQ ID NO:1, SEQ ID NO:3, SEQ ID NO:3 or SEQ ID NO:7. A nucleic acid of the invention can be amplified using cDNA, mRNA or alternatively, genomic DNA, as a template and appropriate oligonucleotide primers according to standard PCR amplification techniques.

In one embodiment, an isolated nucleic acid molecule of the invention is selected from the group consisting of a nucleic acid molecule comprising the nucleotide sequence of SEQ ID NO: 1 or SEQ ID NO: 3, or a complement thereof; and a nucleic acid molecule which encodes a polypeptide comprising the amino acid sequence of SEQ ID NO: 2 or SEQ ID NO: 4.

Isolated Polypeptides

Another aspect of the present invention features isolated RNase A polypeptides (e.g., isolated RNase polypeptides including RNase A-1, RNase A-2, RNase A-2 Domain II polypeptides, RNase A-1 Domain polypeptides, RNase A-2 Domain III polypeptides).

An isolated or purified polypeptide (e.g., an isolated or purified RNase A) is substantially free of cellular material or other contaminating polypeptides from the microorganism from which the polypeptide is derived, or substantially free from chemical precursors or other chemicals when chemically synthesized.

Included within the scope of the present invention are RNase A polypeptides or genes products that are mammalian derived polypeptides or gene products. In a preferred embodiment, the RNase A polypeptide or gene product is derived from the chicken, *Gallus gallus*. In a particular embodiment, the chicken leukocyte RNAse A-1 has been deposited and corresponds to GenBank Accession (DQ39275), and in another particular embodiment, the chicken leukocyte RNAse A-2 has been deposited and corresponding to GenBank Accession (DQ39276). Further included within the scope of the present invention are RNase A polypeptides or gene products that are mammalian and non-mammalian derived polypeptides or gene products which differ from naturally-occurring RNase A genes or polypeptides, for example, genes which have nucleic acids that are mutated, inserted or deleted, but which encode polypeptides substantially similar to the naturally-occurring gene products of the present invention, e.g., comprise a RNase A activity that is bactericidal, bacteriostatic, ribonucleolytic, angiogenic.

In particular embodiments of the invention, the isolated polypeptide encodes chicken leukocyte RNase A-1, having SEQ ID NO: 2:

```
VPTYQDFLRTHVDFPKTSFPNIAAYCNVMMVRRGINVHGR

CKSLNTFVHTDPRNLNTLCINQPNRALRTTQQQLPVTDCK

LIRSHPTCSYTGNQFNHRVRVGCWGGLPVHLDGTFP
```

In other particular embodiments of the invention, the isolated polypeptide encodes chicken leukocyte RNase A-2, having SEQ ID NO: 4:

```
VPTYQDFLYKHMDFPKTSFPSNAAYCNVMMVRRGMTAHGR

CKSFNTFVHTDPRNLNTLCINQPDQALRTTRRHFRITDCK

LIRSHPTCRYSGNQFNRRVRVGCRGGLPVHLDGTSP
```

It is well understood that one of skill in the art can mutate (e.g., substitute) nucleic acids which, due to the degeneracy of the genetic code, encode for an identical amino acid as that encoded by the naturally occurring gene. This may be desirable in order to improve the codon usage of a nucleic acid. Moreover, it is well understood that one of skill in the art can mutate (e.g., substitute) nucleic acids which encode for conservative amino acid substitutions. It is further well understood that one of skill in the art can substitute, add or delete amino acids to a certain degree without substantially affecting the function of a gene product (e.g., a RNase A activity, for example ribonuclease, bactericidal, bacteriostatic, or angiogenic activity) as compared with a naturally-occurring gene product, each instance of which is intended to be included within the scope of the present invention.

In an embodiment of the invention, the isolated nucleic acid molecule of the invention is selected from a nucleic acid molecule comprising the nucleotide sequence of SEQ ID NO: 1 or SEQ ID NO: 3, or a complement thereof. In another embodiment of the invention the nucleic acid molecule encodes a polypeptide comprising the amino acid sequence of SEQ ID NO: 2 or SEQ ID NO: 4.

Included in the scope of the invention are isolated polypeptides (e.g., an isolated RNase A polypeptide, more specifically a chicken leukocyte RNase A-2) that comprise a fragment of a polypeptide comprising the amino acid sequence of SEQ ID NO: 2 or SEQ ID NO: 4, wherein the fragment comprises at least 5-15 contiguous amino acids of SEQ ID NO: 2 or SEQ ID NO: 4 and retains at least one biological activity of the reference polypeptide that is bactericidal, bacteriostatic, or angiogenic.

Also included in the scope of the invention are a variant or naturally occurring allelic variant of a polypeptide comprising the amino acid sequence of SEQ ID NO: 2 or SEQ ID NO: 4, wherein the polypeptide is encoded by a nucleic acid molecule which hybridizes to a complement of a nucleic acid molecule comprising SEQ ID NO: 1 or SEQ ID NO: 3 under stringent conditions.

In other embodiments, an isolated polypeptide of the present invention comprises an amino acid sequence which is a homologue of the at least one of the polypeptides set forth as SEQ ID NO: 2 or SEQ ID NO: 4 (e.g., comprises an amino acid sequence at least about 30-40% identical, advantageously about 40-50% identical, more advantageously about 50-60% identical, and even more advantageously about 90%, 91%, 92%, 93%, 94%, 95%, 96%, 97%, 98%, 99% identical to the amino acid sequence of SEQ ID NO: 2 or SEQ ID NO: 4, and has an activity that is substantially similar to that of the polypeptide encoded by the amino acid sequence of SEQ ID NO: 2 or SEQ ID NO: 4, respectively.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions×100), advantageously taking into account the number of gaps and size of said gaps necessary to produce an optimal alignment.

The comparison of sequences and determination of percent identity between two sequences can be accomplished using a mathematical algorithm. A particular, non-limiting example of a mathematical algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to nucleic acid molecules of the invention. BLAST polypeptide searches can be performed with the XBLAST program, score=50, wordlength=3 to obtain amino acid sequences homologous to polypeptide molecules of the invention. To obtain gapped alignments for comparison purposes, Gapped BLAST can be utilized as described in Altschul et al. (1997) *Nucleic Acids Research* 25(17): 3389-3402. When utilizing BLAST and Gapped BLAST programs, the default parameters of the respective programs (e.g., XBLAST and NBLAST) can be used. Another particular, non-limiting example of a mathematical algorithm utilized for the comparison of sequences is the algorithm of Myers and Miller (1988) *Comput Appl Biosci.* 4:11-17. Such an algorithm is incorporated into the ALIGN program available, for example, at the GENESTREAM network server, IGH Montpellier, FRANCE or at the ISREC server. When utilizing the ALIGN program for comparing amino acid sequences, a PAM120 weight residue table, a gap length penalty of 12, and a gap penalty of 4 can be used.

In another embodiment, the percent identity between two amino acid sequences can be determined using the GAP program in the GCG software package, using either a Blossom 62 matrix or a PAM250 matrix, and a gap weight of 12, 10, 8, 6, or 4 and a length weight of 2, 3, or 4. In yet another embodiment, the percent homology between two nucleic acid sequences can be accomplished using the GAP program in the GCG software package, using a gap weight of 50 and a length weight of 3.

Also included in the scope of the invention are isolated polypeptides comprising a fragment of SEQ ID NO: 2 or SEQ ID NO: 4, wherein the amino acids of the fragment are arranged in any sequence such that the fragment has the bactericidal, bacteriostatic, or angiogenic activity of SEQ ID NO: 2 or SEQ ID NO: 4. In an exemplary embodiment, the fragment is an isolated polypeptide comprising the amino acids T,T,R,R,H,F,R,I,T (SEQ ID NO: 6) in any sequence that has a biological activity that is bactericidal, bacteriostatic, or angiogenic.

In general, the sequence of amino acids can be arranged in any sequence that results in a biological activity that is bactericidal, bacteriostatic, or angiogenic.

It is well understood that also included in the scope of the invention are synthetic or recombinant polypeptides.

According to the invention, the isolated polypeptides may exhibit bactericidal, bacteriostatic, or angiogenic activity. The bactericidal or bacteriostatic activity is against a gram negative or gram positive bacteria. Exemplary bacteria can be selected from *Gluconobacter, Rhizobium, Bradyrhizobium, Alcaligenes, Rhodobacter, Rhodococcus. Azospirillum, Rhodospirillum, Sphingomonas, Burkholderia, Desulfomonas, Geospirillum, Succinomonas, Aeromonas, Shewanella, Halochromatium, Citrobacter, Escherichia, Klebsiella, Zymomonas, Zymobacter, and Acetobacter, Fibrobacter, Acidobacter, Bacteroides, Sphingobacterium, Actinomyces, Corynebacterium, Nocardia, Rhodococcus, Propionibacterium, Bifidobacterium, Bacillus, Geobacillus, Paenibacillus, Sulfobacillus, Clostridium, Anaerobacter, Eubacterium, Streptococcus, Lactobacillus, Leuconostoc, Enterococcus, Lactococcus, Thermobifida, Cellulomonas, and Sarcina* (e.g. *Sarcina ventriculi*). In particular embodiments of the invention the isolated polypeptides may exhibits bactericidal or bacteriostatic activity against *Escherichia, Salmonella, Bacillus, Streptococcus*, and *Staphylococcus* bacterium. In particular, an isolated polypeptide with bactericidal or bacteriostatic activity according to the invention is useful against a natural pathogen, for example *Salmonella enterica*.

Based on the foregoing isolated RNase A polypeptides, immunospecific antibodies can be raised against a RNase A polypeptides, or portions thereof, using standard techniques known in the art and as described further in the methods herein.

Antibodies

Antibodies are well known to those of ordinary skill in the science of immunology. As used herein, the term "antibody" means not only intact antibody molecules, but also fragments of antibody molecules that retain immunogen binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments which lack the Fc fragment of intact antibody, clear more rapidly from the circulation, and may have less non-specific tissue binding of an intact antibody (Wahl et al., *J. Nucl. Med.* 24:316-325 (1983).

Examples of antibodies include monoclonal antibodies, polyclonal antibodies, the preparation and use of which are known to the skilled artisan. Other exemplary antibodies include whole native antibodies, bispecific antibodies, Fab, Fab', single chain V region fragments (scFv) and fusion polypeptides. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing RNase A polypeptides (e.g., RNase A-1, RNase A-2), or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding an RNase A polypeptide (e.g., RNase A-1, RNase A-2), or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding an RNase A polypeptide (e.g., RNase A-1, RNase A-2), or immunogenic fragments thereof, can be expressed in cells in vitro, followed by isolation of the receptor and administration of the receptor to a suitable host in which antibodies are raised.

Using either approach, antibodies can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition; e.g., Pristane.

Monoclonal antibodies (Mabs) can be prepared "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

In particular embodiments of the invention, an antibody is used to detect *Gallus gallus* leukocyte RNase A-1. In another embodiment, an antibody is used to detect *Gallus gallus* leukocyte RNase A-2. The antibody can be prepared against any sequence of RNase A-1 or RNase A-2 using techniques discussed and known to one of ordinary skill in the art. In one example, to detect RNase A-1, the antibody can be prepared against the sequence QPNRALRTTQQQLP (SEQ ID NO: 9). In another example, to detect RNase A-2, the antibody can be prepared against the sequence DQALRTTRRHFRIT (SEQ ID NO: 10).

Methods of Treatment

Included in the scope of the invention are isolated RNase A polypeptides and fragments that have bactericidal activity. Thus, the methods of the invention comprise treatment of bacterial infection in a mammal suffering from or susceptible to the bacterial infection, comprising selecting a mammal that is suffering from or susceptible to bacterial infection and administering to the selected mammal a therapeutically effective amount of a RNase A polypeptide or fragment thereof.

RNase A polypeptides and fragments according to the invention that have bactericidal activity are particularly preferred for use in the treatment methods of the invention. The bactericidal and bacteriostatic activity of a particular RNase A polypeptides or fragments can be assessed by known protocols, such as that described in the methods section and the following described protocol, herein referred to as "a standard bacterial colony formation assay." Bactericidal assays are well-described in the art, and are performed as described previously [28], and as exemplified in Examples 3-6. Briefly, an aliquot from a single bacterial colony overnight culture grown in Luria-Beitani (LB) broth is diluted 1:100 in sodium phosphate, pH 7.4, collected by centrifugation, and resuspended in sodium phosphate, pH 7.4. An aliquot of bacteria in buffer are incubated for 4 hr at 37° C. with recombinant protein or peptide at concentrations indicated, or diluent control and were then diluted 10, 100, or 1000-fold prior to plating on LB agar for overnight growth for colony counts.

Also included in the scope of the invention are isolated RNase A polypeptides and fragments that have angiogenic activity. Angiogenic activity may be important in, for example, wound healing or tissue repair. Clinically, wounds or skin ulcerations associated with diabetes or burn wounds that are caused by impaired blood supply can be treated with therapeutic angiogenic promoters. Thus, the methods of the invention comprise treatment of conditions of impaired blood supply in a mammal suffering from or susceptible to conditions of impaired blood supply, comprising selecting a mammal that is suffering from or susceptible to conditions of impaired blood supply, and administering to the selected mammal a therapeutically effective amount of a RNase A polypeptide or fragment thereof.

The angiogenic activity of a particular RNase A polypeptide or fragment can be assessed by known protocols, such as that described in the methods section and the following described protocol, herein referred to as "a standard angiogenesis assay." For example, the chick aortic ring sprouting assay, described in the art [33], can be a standard angiogenesis assay according to the invention. In the assay, aortic arches are dissected from 13-day-old chicken embryos, cleaned free of unwanted tissue and cut into 0.8 mm slices. Each ring is transferred into center of a well of 96-well plate, and ice-cold Matrigel (Becton Dickinson, Bedford, Mass.) is added immediately to imbed the ring. After solidification of the Matrigel, human endothelial-SFM basal growth medium (Invitrogen) is added to each well. After addition of recombinant leukocyte RNase A-1 or RNase A-2 or control preparation, the rings are incubated at 37° C. for 24 h. Vessels sprouted from rings are observed under microscopy, and assessed by blinded observers.

Pharmaceutical Compositions and Administration

The present invention contemplates pharmaceutical preparations comprising a RNase A polypeptide and fragments thereof, together with a pharmaceutically acceptable carrier. Polypeptides of the invention may be administered as part of a pharmaceutical composition. The compositions should be sterile and contain a therapeutically effective amount of the polypeptides in a unit of weight or volume suitable for administration to a subject.

These compositions ordinarily will be stored in unit or multi-dose containers, for example, sealed ampoules or vials, as an aqueous solution or as a lyophilized formulation for reconstitution. As an example of a lyophilized formulation, 10 mL vials are filled with 5 mL of sterile-filtered 1% (w/v) aqueous RNase A polypeptide solution, such as an aqueous solution of RNase A-2 Domain II polypeptide, and the resulting mixture can then be lyophilized. The infusion solution can be prepared by reconstituting the lyophilized material using sterile Water-for-Injection (WFI).

The RNase A polypeptide, or fragment, may be combined, optionally, with a pharmaceutically acceptable excipient. The term "pharmaceutically-acceptable excipient" as used herein means one or more compatible solid or liquid filler, diluents or encapsulating substances that are suitable for administration into a human. The term "carrier" denotes an organic or inorganic ingredient, natural or synthetic, with which the active ingredient is combined to facilitate administration. The components of the pharmaceutical compositions also are capable of being co-mingled with the molecules of the present invention, and with each other, in a manner such that there is no interaction that would substantially impair the desired pharmaceutical efficacy.

The compositions can be administered in effective amounts. The effective amount will depend upon the mode of administration, the particular condition being treated and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

With respect to a subject having a bacterial infection, an effective amount is sufficient to stabilize, slow, or reduce the bacterial infection. With respect to a subject in need of treatment to increase angiogenesis, an effective amount is sufficient to increase the formation of new blood vessels. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate levels of the polypeptide compositions of the present invention.

A variety of administration routes are available. The methods of the invention, generally speaking, may be practiced using any mode of administration that is medically acceptable, meaning any mode that produces effective levels of the active compounds without causing clinically unacceptable adverse effects. A particular mode of administration includes topical administration. Compositions comprising a therapeutic composition which are suitable for topical administration can take one of several physical forms, such as a liquid, including a tincture or lotion, which may be applied by pouring, dropping or "painting" (i.e. spreading manually or with a brush or other applicator such as a spatula) or injection. Topical administration may take the form of an ointment or cream, a dry powder, which may be shaken or sifted onto the target tissue or, alternatively, applied as a nebulized spray, a liquid-based aerosol, which may be dispensed from a container selected from the group that comprises pressure-driven spray bottles (such as are activated by squeezing), natural atomizers (or "pump-spray" bottles that work without a compressed propellant) or pressurized canister. Note that in some cases, if the surface in question is internal, topical application would comprise taking the therapeutic composition via an oral route, whether in liquid, gel or solid form.

Another particular mode of administration includes systemic administration. Systemic administration of a therapeutic composition according to the invention may be performed by methods of whole-body drug delivery, and are well known in the art. These include, but are not limited to, intravenous drip or injection, subcutaneous, intramuscular, intraperitoneal, intracranial and spinal injection, ingestion via the oral route, inhalation, trans-epithelial diffusion (such as via a drug-impregnated, adhesive patch) or by the use of an implantable, time-release drug delivery device. Systemic administration is advantageous when a pharmaceutical composition must be delivered to a target tissue that is widely-dispersed, inaccessible to direct contact or, while accessible to topical or other localized application, is resident in an environment (such as the digestive tract) wherein the native activity of the nucleic acid or other agent might be compromised, e.g. by digestive enzymes or extremes of pH.

A therapeutic composition of use in the invention can be given in a single- or multiple dose. A multiple dose schedule is one in which a primary course of administration can include 1-10 separate doses, followed by other doses given at subsequent time intervals required to maintain and or reinforce the level of the therapeutic agent. Such intervals are dependent on the continued need of the recipient for the therapeutic agent, and/or the half-life of a therapeutic agent. The efficacy of administration may be assayed by monitoring the reduction in the levels of a symptom indicative or associated with the disease it is designed to target, for example the inhibition of bacterial infection. The assays can be performed as described herein or according to methods known to one skilled in the art.

A therapeutically effective regimen may be sufficient to arrest or otherwise ameliorate symptoms of a disease. An effective dosage regimen requires providing the regulatory drug over a period of time to achieve noticeable therapeutic effects wherein symptoms are reduced to a clinically acceptable standard or ameliorated. The symptoms are specific for the disease in question. For example, when the disease is associated with bacterial infection, such as to treat infections of the skin, open wounds, burn wounds, or systemic infection, the claimed invention is successful when the bacterial infection is reduced by at least 20%, and preferably reduced by 30%, 40% or 90%. When the disease is associated with impaired blood supply, or is at risk of developing a condition of impaired blood supply, such as wound healing, the claimed invention is successful when the angiogenesis is increased by at least 5%, and preferably increased by 10%, 20% or 30%. Angiogenesis can be measured by any standard angiogenesis assay, such as the chick aortic ring sprouting assay, the in vivo Matrigel plug and corneal neovascularization assays, the in vivo/in vitro chick chorioallantoic membrane (CAM) assay, and the in vitro cellular (proliferation, migration, tube formation) and organotypic (aortic ring) assays, as described in Auerbach et al., Clinical Chemistry. 2003, and incorporated herein by reference in its entirety.

This invention is further illustrated by the following examples, which should not be construed as limiting. All documents mentioned herein are incorporated herein by reference.

EXAMPLES

Abbreviations used are as follows: ECP, eosinophil cationic protein; EDN, eosinophil-derived neurotoxin; RNase, ribonuclease; RNase-superfamily-related (RSFR); PR1, placental ribonuclease inhibitor, Example 1

RNase a Ribonucleases in the Genome of the Domestic Chicken, *Gallus gallus*

Three RNase A ribonucleases have been identified in the genome of the chicken, *Gallus gallus* [11]. FIG. 1 is an unrooted neighbor-joining tree that compares these three chicken sequences to other known non-mammalian and mammalian RNase A ribonucleases. The tree indicates three things: (1) these three sequences are most closely related to one another (2) the sequences are more closely related to the other known non-mammalian RNase A ribonucleases than to any of the mammalian superfamily members, and (3) together, the non-mammalian RNase superfamily members are most closely related to the mammalian angiogenin lineage, which, as noted by Cho et al. [11], likely represents the ancestral structural subtype of this superfamily. Full-length cDNAs of the two chicken leukocyte RNases were re-isolated by RT-PCR from RNA prepared from bone marrow of white Leghorn chickens (*Gallus gallus*). The full-length sequences of the two RNases were deposited into GenBank as chicken leukocyte RNase A-1 (ATCC deposit #DQ395275) and chicken leukocyte RNase A-2 (ATCC deposit #DQ395276). These sequences share 93% nucleotide sequence identity to one another and are identical to RNase A/angiogenin [19] and RNase-superfamily-related (RSFR) [20], respectively. The new names are more consistent with current RNase A family nomenclature, and make no specific assumptions vis à vis gene function. The chicken leukocyte RNase A-1 and A-2 map to chromosome 6 (GenBank NW_060392), and are separated by only 10 Kb. The signal sequences are 100% identical; the ratio of rates of non-synonymous ($d_N$=n/N=0.095) to synonymous ($d_S$=s/S=0.055) substitution calculated for the mature coding sequence is >1.0 ($d_N/d_S$=1.73), thus suggesting divergence by positive (Darwinian) selection.

Example 2

Figure 2B:
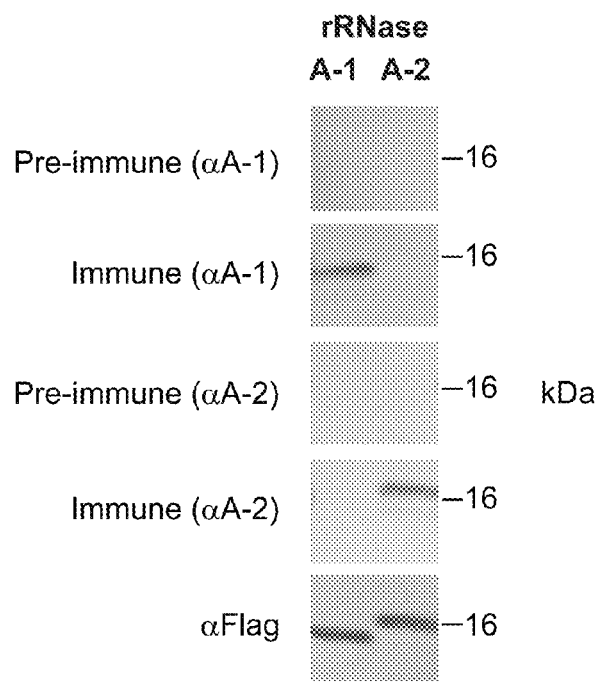
FIGS. 2 (A-D) depict the amino acid sequences of RNase A-1 and RNAse A-2 in panel (A), Western blots in panels (B) and (C), and immunolocalization of RNases A-1 and A-2 in panel (D). In panel (A), the amino acid sequences of RNase A-1 and RNase A-2 (minus amino-terminal signal sequences) are as shown, which document 81% sequence identity, six structural cysteines (C), catalytic histidines 11 and 110 (in boxes), and catalytic lysine 42 (in box) within an invariant CKXXNTF (SEQ ID NO: 14) region (shown in the in larger box), an RNase A family signature motif, is shown. Amino acid sequence differences are indicated with italics. Rabbit anti-peptide antisera were prepared against KLH-conjugated peptides A1 (overlined; $NH_2$-QQQLPV-COOH, SEQ ID NO: 15) and A2 (underlined; $NH_2$-RRHFR1-COOH, (SEQ ID NO: 16) as shown. Panel (B) shows characterization of the specificity of the anti-peptide antibodies against recombinant carboxy-terminal FLAG-tagged RNase (rRNase) A-1 and A-2 by Western blot. Antibodies used for blotting are listed to the left of the blot. The lanes are labeled as rRNase A-1 or A-2. The two panels of (C) are showing detection of RNase A-1 and RNase A-2 in bone marrow and peripheral blood granulocytes by Western blot. The left panel shows blotting with anti A-1 anti-body, and the right panel shows blotting with anti-A-2 antibody. The sample that was used is indicated on the bottom of the panel. (D) comprises four panels (i-iv) showing immunolocalization of RNases A-1 and A-2 in bone marrow (panels i. and ii.) and peripheral blood granulocytes (panels iii. and iv.). Cytospin preparations were probed with primary antibody followed by FITC-conjugated goat anti-rabbit IgG (green), or DAPI (blue); merged images shown, original magnification, 63×.
Figure 2C:
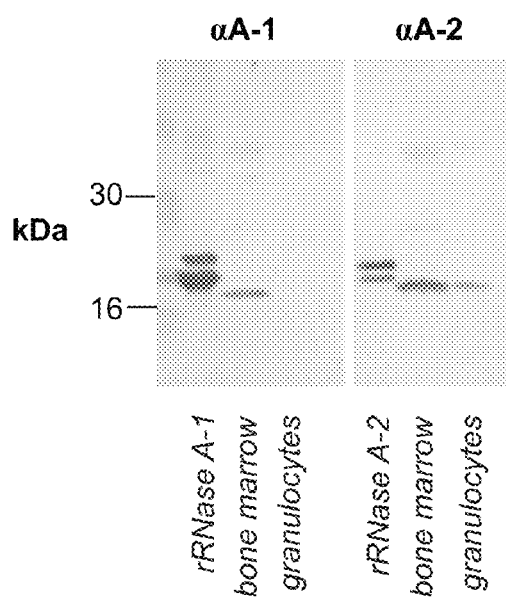
Figure 2D:
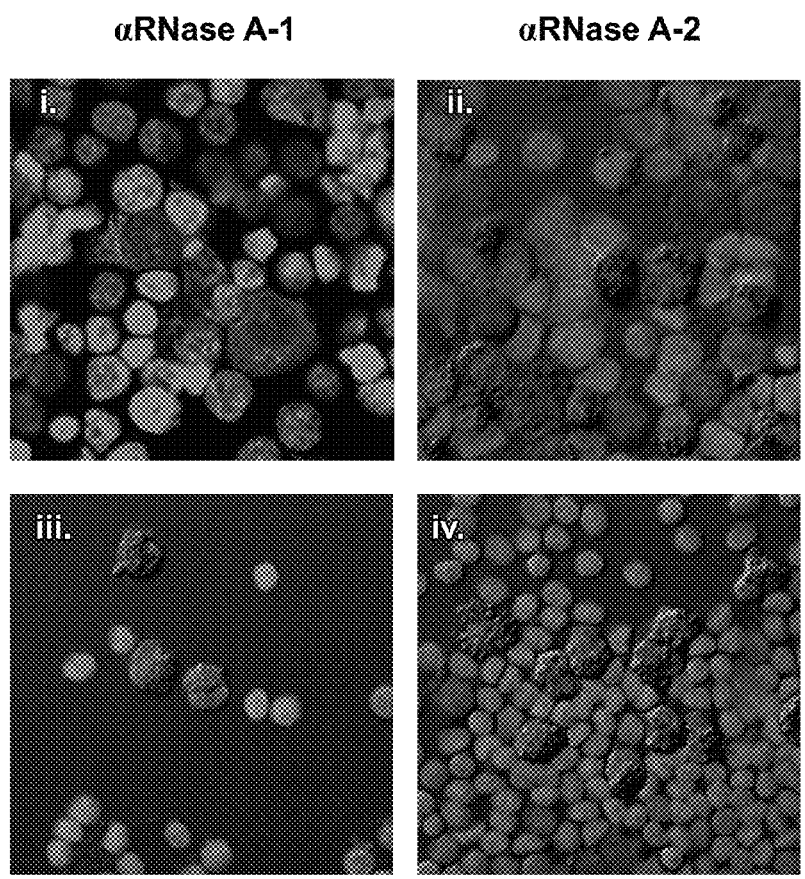

Detection and Characterization of Leukocyte RNases A-1 and A-2 in Bone Marrow and Peripheral Blood Granulocytes The amino acid sequences of leukocyte RNases A-1 and A-2 are shown in FIG. 2A. The sequences are shown without the encoded 23 amino acid signal sequences. The amino termini were determined by direct analogy with the amino terminus of the paralogous chicken RNase CL2 (PDB accession number AAB28438), which was determined by Irie et al. directly from protein sequence [21]. The amino acid sequences (without signal sequences) of RNase A-1 and A-2 are 81% identical, although the isoelectric point of leukocyte RNase A-1 is 10.2, and that of RNase A-2 is 11.0, the divergence due to the extra arginines (10 vs. 14) in the RNase A-2 sequence. Each sequence includes canonical features of the RNase A superfamily, including six cysteines, which is characteristic of the angiogenin-type RNase A ribonucleases, the catalytic histidines (at positions 11 and 110 as shown in FIG. 2A) and the catalytic lysine at position 42 within the CKXX-NTF signature motif. Rabbit antibodies were prepared against divergent peptides shown in FIG. 2A included anti-A-1, QPNRALRTTQQQLP (SEQ ID NO: 9); anti-A-2, DQALRRTRRHFRIT (SEQ ID NO: 10). The antibodies were evaluated for activity and specificity by immunoblotting against recombinant carboxy-terminal FLAG-tagged recombinant leukocyte RNase A-1 and A-2, as shown in FIG. 2B. Pre-immune sera, used as control, did not detect either recombinant RNase A-1 or A-2. A 1:200 dilution of anti-A-1 antibody detected RNase A-1 only, and a 1:200 dilution of anti-A-2 antibody detected RNase A-2 only. Both proteins were readily detected with the anti-FLAG antibody control. Using these antibodies, ~16 kDa immunoreactive bands corresponding to leukocyte RNase A-1 and RNase A-2 were detected in chicken bone marrow lysates, as reported in FIG. 2C. Only RNase A-2 was detected in the lysates from peripheral blood granulocytes. Both immunoreactive RNase A-1 and RNase A-2 were detected in the cytoplasm of cells in the bone marrow. Both RNase A-1 and RNase A-2 were detected in ~80% of peripheral blood granulocytes, as shown in FIG. 2D. No positive cells were detected using preimmune sera.

Example 3

Activity of Recombinant Leukocyte RNases

Angiogenic

Figure 3A:
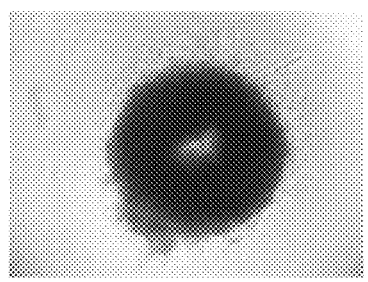
FIGS. 3 A-C are photographs showing the angiogenic activity of recombinant leukocyte RNases.
Figure 3B:
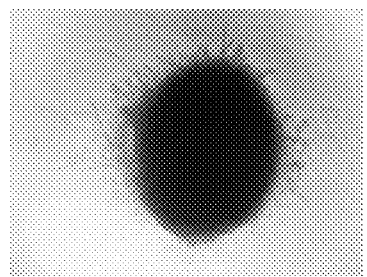
Figure 3B:
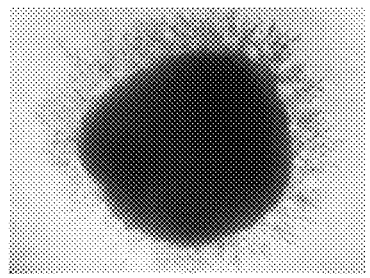

Both chicken leukocyte RNases are structurally related to the mammalian angiogenin lineage, as discussed above and illustrated in FIG. 1. However, none of the non-mammalian ribonucleases evaluated thus far have been reported to have angiogenic activity. Here, the potential angiogenic activity of recombinant leukocyte RNases A-1 and A-2 was evaluated using the chick aortic ring assay as described in the literature [33]. Briefly, aortic rings prepared from 13 day-old chick embryos were incubated with 2 µM recombinant leukocyte RNases (rRNases). Prominent blood vessel formation was observed in the rings incubated with leukocyte rRNase A-2, as shown in FIG. 3 and Table 1, below. Table 1.

TABLE 1

Angiogenesis Scores

Arbitary Units (Mean ± SEM)

| | Control | rRNase A-1 | % change | rRNase A-2 | % change |
|---|---|---|---|---|---|
| Exp. 1 | 0.37 ± 0.07 | 0.38 ± 0.13 | +2.7 | 0.68 ± 0.26* | +84 |
| Exp. 2 | 0.33 ± 0.06 | 0.41 ± 0.06 | +24 | 0.60 ± 0.14* | +82 |

Table 1 details the results of the chick aortic ring assay. Specifically, vessels sprouted from aortic rings treated with 100 µl of human endothelial-SFM basal growth medium and 2 µM recombinant leukocyte RNase were observed under microscopy and assessed by blinded observers, according previously published methods [33]. Each of the groups (named Exp. 1 and Exp. 2) were composed of 6 to 8 rings. Percent (%) change is a value that represents ([rRNase A-1 or A-2−control]×100/[control]). *p<0.05, as determined using the Student's t-test.

The blood vessel formation in aortic rings exposed to 2 µM leukocyte rRNase A-1 was comparable to that in the control (vector only transfectant) protein preparations. Thus, this data shows that leukocyte rRNase A-2, but not rRNase A-1, has angiogenic activity ex vivo.

Enzymatic

Figure 4A:
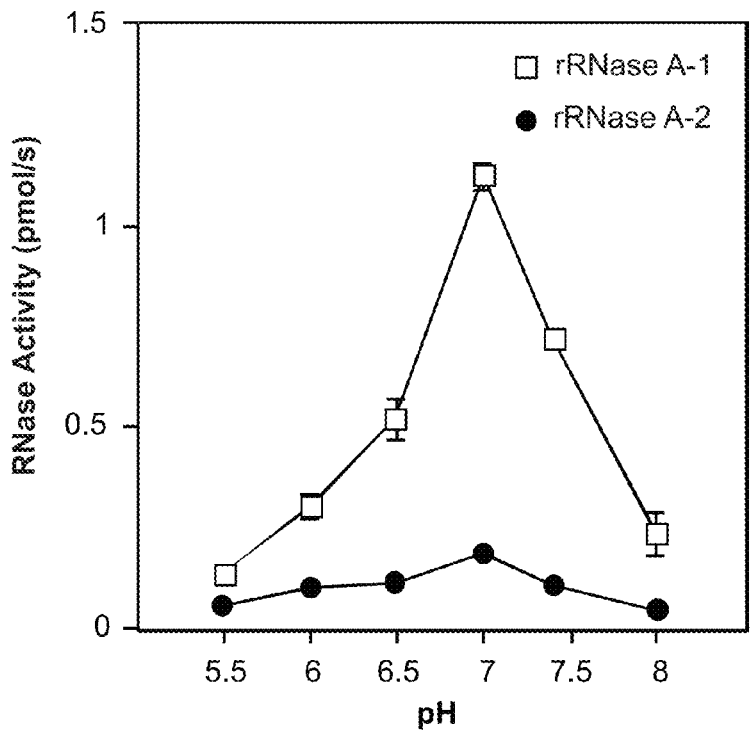
FIGS. 4 A-D are graphs showing the ribonucleolytic activity of recombinant leukocyte RNases. (A) is a graph showing the optimum pH for RNase activity. Enzymatic activity was determined with 50 pmol rRNase A-1 (open squares) and rRNase A-2 (closed circles) that was incubated with 250 μg/ml yeast tRNA in 40 mM sodium phosphate buffer at the pHs indicated. Measurements of $A_{260}$ per time were converted to pmol/s as described in reference 28 and Methods. (B) is a graph showing the initial rates for RNase activity. Enzymatic activity was determined as described in (A) with 40 mM sodium phosphate buffer, pH 7.0. (C) is a graph showing the substrate preference for RNase activity. 50 pmol rRNase A-1 (left panel) and rRNase A-2 (right panel) proteins were incubated with 250 μg/ml of poly U (open squares), poly C (closed circles), poly A (open diamonds), poly G (open triangles) and poly I (open circles) in 40 mM sodium phosphate buffers, pH 7.0. $A_{260}$ was measured after precipitation of undigested RNA at each of the time points indicated. (D) is two panels of graphs showing interaction of RNase with human placental RNase inhibitor (hPR1). RNase activity was measured with 10 µmol of bovine pancreatic RNase (left) or 50 µmol rRNase A-1 and rRNase A-2 (right) with 250 µg/ml of yeast tRNA as substrate with (+) or without (−) 200 U human placental RNase inhibitor (hPR1) in 40 mM sodium phosphate buffer, pH 7.0. The hPR1 was added to the RNases in buffer 5 min prior to initiation of RNase assay by addition of substrate. *p<0.01.
Figure 4B:
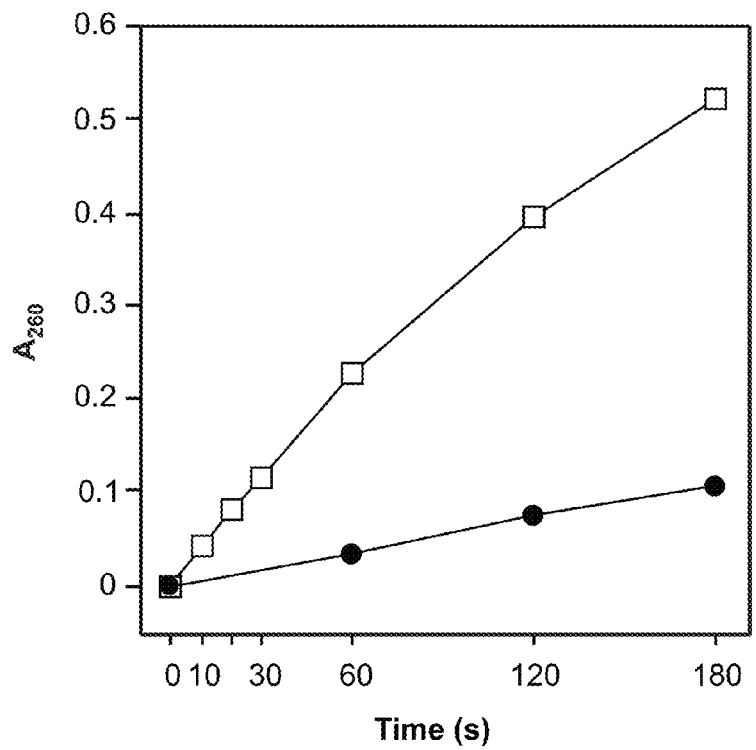

Next, the enzymatic activity of the two recombinant leukocyte RNases was characterized. Optimum pH was determined as 7.0 with 50 pmol rRNase A-1 or A-2, with 200 µg yeast tRNA substrate in 40 mM sodium phosphate buffers ranging from pH 5.5 to 8.0, as shown in FIG. 4A. Both rRNase A-1 and rRNase A-2 demonstrated optimal activity at pH 7.0; thus all further activity measurements were performed at pH 7.0. Table 2, below, shows the enzymatic constants $K_m$ and $k_{cat}$ were determined using the yeast tRNA substrate based on linear initial rates, and FIG. 4B shows the enzymatic constants $K_m$ and $k_{cat}$ for rRNase A-1 and rRNase A-2 (50 pmol, 40 mM sodium phosphate buffer, pH 7.0, yeast tRNA substrate). Enzymatic activity was measured using 10 pmol rRNase A-1 or rRNase in 40 mM sodium phosphate buffer, pH 7.0. Conversion from $A_{260}$ to pmol ribonucleotide product was carried out as described in reference 29 and in the Methods. Although the value for $k_{cat}$ ($s^{-1}$) for RNase A-2 was 50-times lower than that for RNase A-1, the value determined for $K_m$ (M) for chicken leukocyte RNase A-2 was 34 times lower than that for RNase A-1, which resulted in comparable catalytic efficiencies ($k_{cat}/K_m$ ($M^{-1}s^{-1}$)).

TABLE 2

Enzymatic constants determined for recombinant *Gallus gallus* RNases.

| Enzyme | $K_m$ (µM) | $k_{cat}$ ($sec^{-1}$) | $k_{cat}/K_m$ ($M^{-1}sec^{-1}$) |
|---|---|---|---|
| rRNase A-1 | 17.2 | 2.61 | $1.5 \times 10^5$ |
| rRNase A-2 | 0.5 | 0.056 | $1.1 \times 10^5$ |

Figure 4C:
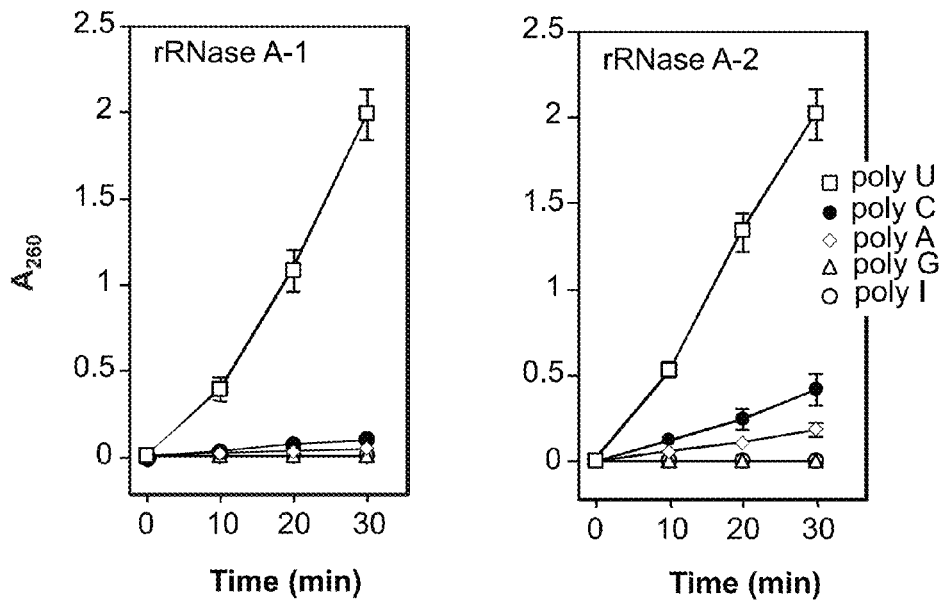

Recombinant leukocyte RNases A-1 and A-2 hydrolyzed poly U RNA, at initial rates that were roughly equivalent to one another, as shown in the graph in FIG. 4C. Polyribonucleotides other than poly U were poor substrates for leukocyte rRNase A-1. Recombinant RNase A-2 cleaved poly C and poly A, although at initial rates that were lower than those observed for poly U. Neither of the leukocyte RNases cleaved poly G, poly I, or double-stranded RNA.

Figure 4D:
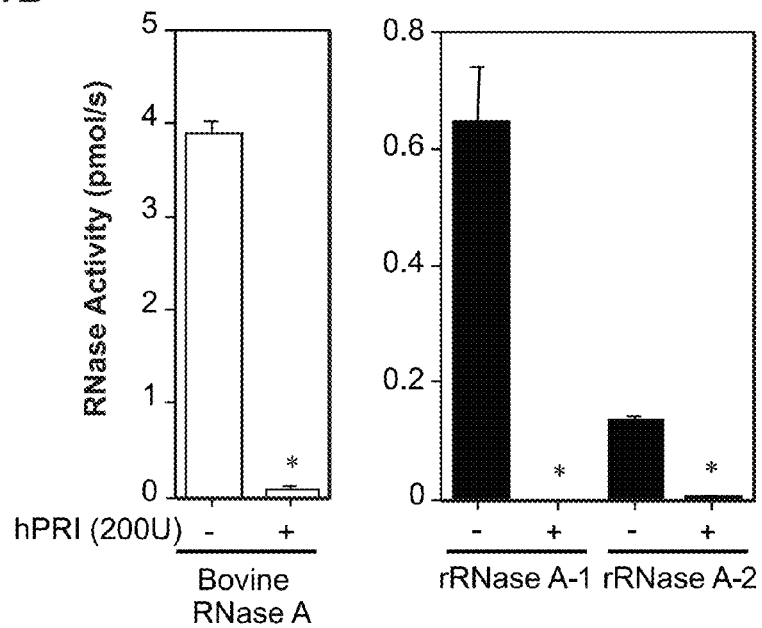

FIG. 4D shows that even given the large evolutionary distance between species, preincubation with 200 U human placental RNase inhibitor (hPRI) completely inhibited RNase activity of both *Gallus gallus* leukocyte RNases.

Bactericidal

Figure 5A:
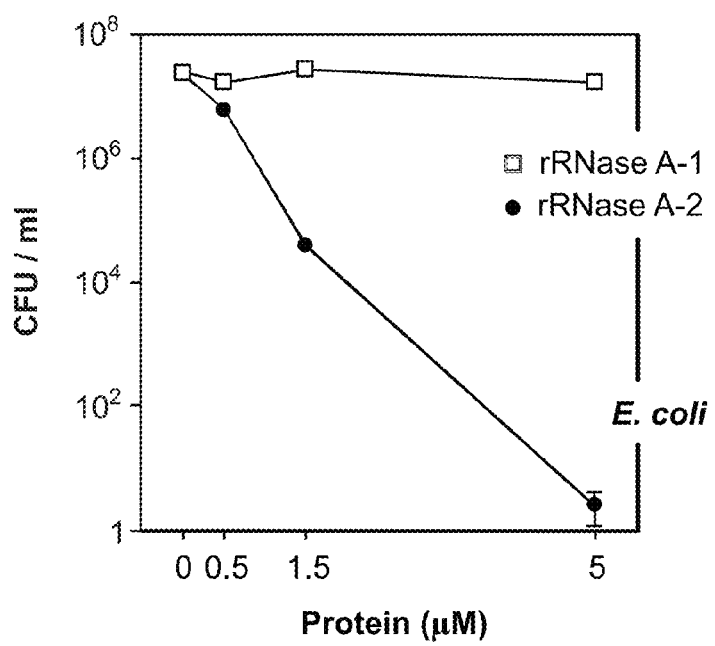
FIGS. 5 A & B are graphs showing the bactericidal activity of rRNases A-1 and A-2. In panel (A) *E. coli* DH5α and in panel (B) *S. aureus* 502A were re-suspended in 100 mM sodium phosphate buffer, pH 7.4, and incubated with the indicated concentrations of chicken leukocyte RNase A-1 (open squares) and A-2 (closed circles) for 4 h at 37° C., plated on RNase-free LB agar, and grown overnight for colony counts.
Figure 5B:
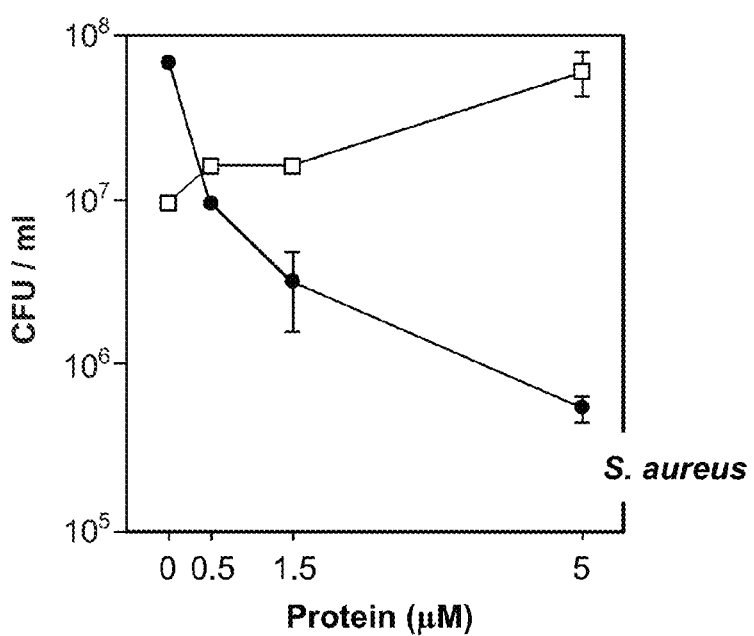

The human eosinophil cationic protein (ECP)/RNase 3, human RNase 7, and mouse angiogenin-4 all demonstrate antibacterial activity [28, 35-37]. Next, the bactericidal activity of chicken leukocyte RNases were examined using a colony-forming assay as previously described for eosinophil cationic protein [28]. FIG. 5 shows that colony formation of *Escherichia coli* and *Staphylococcus aureus* was reduced in a dose-dependent fashion in response to incubation with leukocyte rRNase A-2 prior to plating on RNase-free LB medium. *E. coli* was more susceptible to the bactericidal activity of leukocyte rRNase A-2 than was *S. aureus*, as 5 µM rRNase A-2 reduced the colony count of *E. coli* $10^7$-fold, while reducing the colony count of *S. aureus*, only 100-fold. Recombinant RNase A-1 had no effect on colony number of *E. coli* or *S. aureus* concentrations up to and including 5 µl %/l.

Together, these data show that: (1) leukocyte rRNase A-2, but not rRNase A-1, has angiogenic activity ex vivo, (2) the initial rates catalyzed by rRNase A-1 are significantly more rapid than those catalyzed by rRNase A-2, and (3) rRNase A-2 has bactericidal activity that rRNase A-1 does not.

Example 4

Domain Exchange Mutants of rRNAses A-1 and A-2

Preparation of Domain-Exchange Mutants of rRNases A-1 and A-2.

Figure 6A:
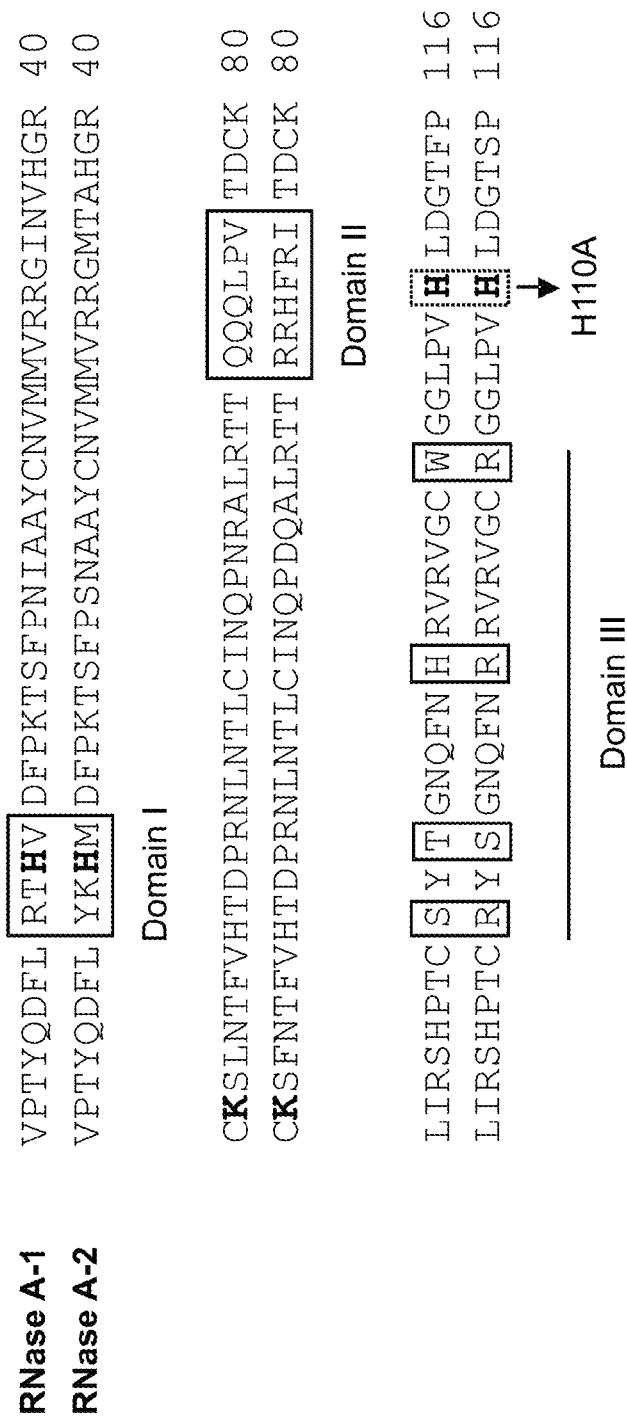
FIGS. 6 A & B show the identification of the divergent domains within the *Gallus gallus* leukocyte RNase A-1 and A-2 sequences and the exchange mutation strategy. Panel (A) shows the mature amino acid sequences of chicken leukocyte RNases A-1 and A-2. The divergent amino acids are enclosed in boxes and domains I, II and III as indicated. Likewise boxed is catalytic histidine 110. Panel (B) shows the strategies for creating domain-exchange mutants of RNases A-1 and A-2. Independent ribonuclease-minus forms of rRNase A-1 and rRNase A-2 are created by point mutation of $H^{110}$ to alanine (H110A).

Next, to identify the amino acid sequences that have a direct impact on these biological activities, rRNases were prepared in which three specific divergent domains (domains I, II, and III) were exchanged. FIG. 6A shows the mature amino acid sequences of chicken leukocyte RNases A-1 and A-2. The divergent amino acids are enclosed in boxes and domains I, II and III as indicated. FIG. 6B documents the amino acid substitutions that contributed to the specific domain exchanges between leukocyte rRNase A-1 and A-2. In addition to these exchanges, a mutation at $His^{110}$ to Ala was introduced, which disrupts the catalytic triad (refer to FIG. 2A) in order to provide an independent assessment of RNase activity and its role in the bactericidal activity observed.

Enzymatic and Bactericidal Activity of Domain-Exchange Mutants of rRNase A-1.

Figure 7A:
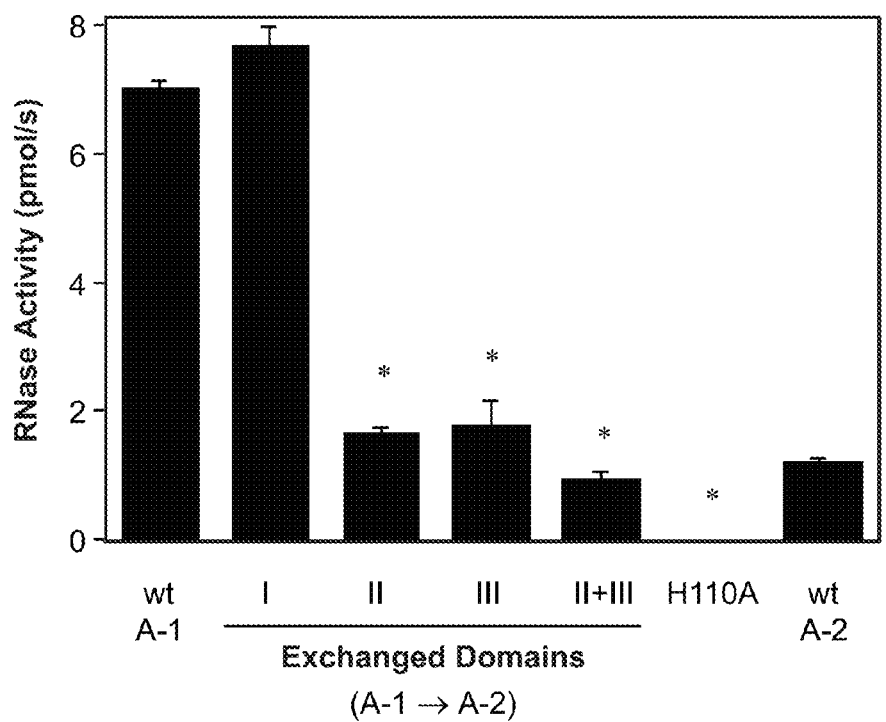
FIGS. 7 A & B are graphs showing the biological activity of rRNase A-1 and exchange mutants including domains I, II and III from RNase A-2. Panel (A) shows RNase activity. Enzymatic activity was measured as described in Legend to FIG. 4 and Methods; values are the means±SEM from three independent experiments. *p<0.01 vs. wild type A-1. Panel (B) shows Bactericidal activity. As described in the legend to FIG. 5 and in the Methods, *E. coli* were incubated with 5 µM chicken leukocyte RNases for 4 hrs and re-plated for colony counts. Values are the means±SEM from three independent experiments. *p<0.01 vs. wild type A-1.

The data in FIG. 7A document the RNase activity of domain-exchange mutants of rRNase A-1. Initial rates of RNase activity were measured with 50 pmol recombinant rRNase for 1 min (refer to FIG. 4B). Substitution of domain II, III, or II and III of rRNase A-2 significantly reduced the activity of the RNase A-1 backbone to a level indistinguishable from that of rRNase A-2 itself. Substitution of $His^{110}$ to Ala completely eliminated RNase activity.

Figure 7B:
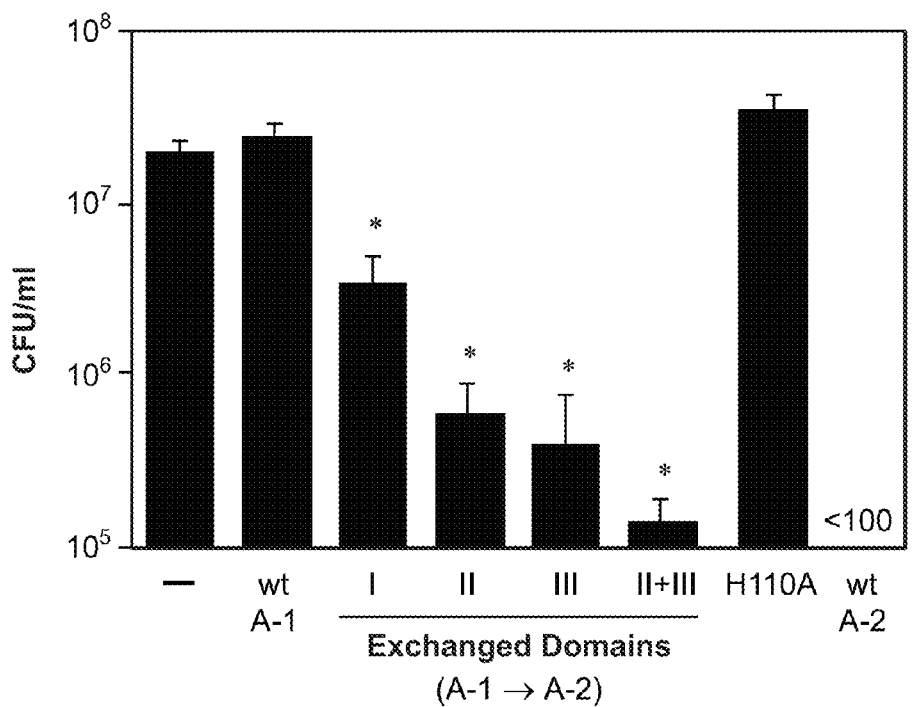

FIG. 7B addresses the bactericidal activity of the domain-exchanged mutants of rRNase A-1 against *E. coli*. Each protein was tested at 5 µM, which is sufficient for RNase A-2 to exert a $10^7$-fold reduction in colony count (refer to FIG. 5). In accord with earlier results, the presence of wild type rRNase A-1 had no impact on colony count, while rRNase A-2 reduced the colony count to fewer than 100 colony forming units (CFU)/ml. Substitution of the RNase A-1 backbone with either domain I, and more so, II or III, of RNase A-2 conferred bactericidal activity on RNase A-1. Furthermore, substitution with domains II and III together resulted in a protein capable of reducing the *E. coli* colony count by 100-fold (p<0.01).

Enzymatic and Bactericidal Activity of Domain-Exchange Mutants of Chicken Leukocyte RNase A-2.

Figure 8A:
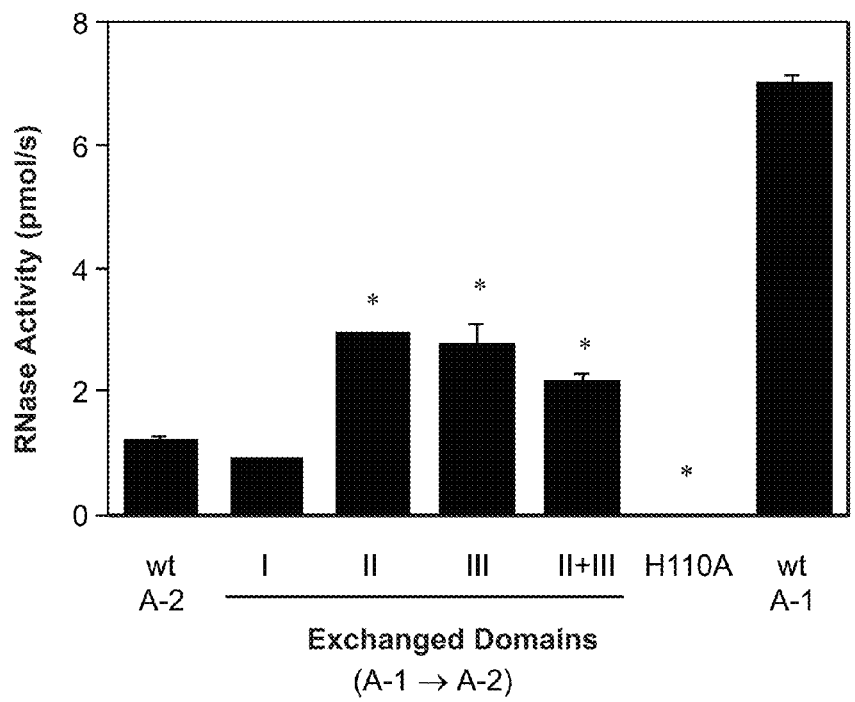
FIGS. 8 A & B are graphs showing the biological activity of rRNase A-2 and exchange-mutants including domains I, II and III from RNase A-1. Panel (A) shows RNase activity. Enzymatic activity was measured as described in Legend to FIG. 4 and Methods; values are the means±SEM from three independent experiments. *p<0.01 vs. wild type A-2. Panel (B) shows bactericidal activity. As described in the legend to FIG. 5 and in the Methods, *E. coli* were incubated with 5 µM chicken leukocyte RNases for 4 hrs and re-plated for colony counts. Values are the means±SEM from three independent experiments. *p<0.01 vs. wild type A-2.

The RNase activities of domain-exchange mutants of rRNase A-2 were measured under the same conditions as those of rRNase A-1. Substitution of domain II or III or domains II and III together of rRNase A-1 all augmented the RNase activity of rRNase A-2, although the activities of these domain-exchanged mutants were less than that of wild type rRNase A-1, as shown in FIG. 8A. Similar to results obtained for rRNase A-1, substitution of $His^{110}$ to Ala completely abolished RNase activity.

Figure 8B:
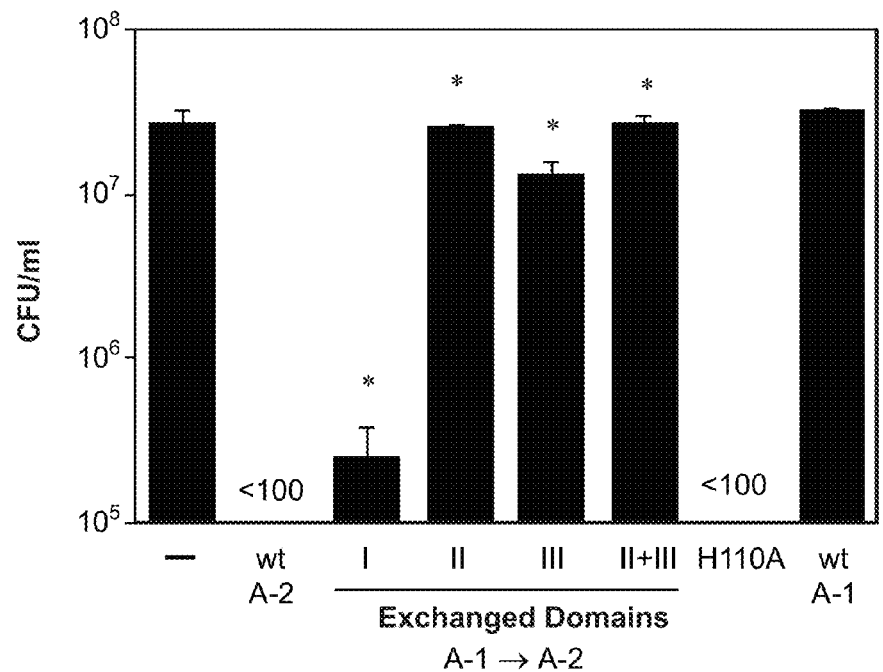

Bactericidal activities of rRNase A-2 domain-exchanged mutants are shown in FIG. 8B. rRNase A-2 reduced the colony count to fewer than 100 CFU/ml. Of note, the $His^{110}$-Ala ribonucleases(−)minus mutant form was also bactericidal and equally active as the wild type form, indicating that ribonuclease activity can be decoupled from bactericidal activity. Substitution of domain I of rRNase A-1 onto the rRNase A-2 backbone significantly attenuated bactericidal activity. Further, substitution of either domain II or III of rRNase A-1 alone, or domains II and III together, eliminated the bactericidal activity of RNase A-2.

Taken together, these data show that substitution of domains II and III of rRNase A-2 confer bactericidal activity on RNase A-1. Removal of these domains from rRNase A-2 eliminate bactericidal activity. Further, ribonuclease activity per se is not at all essential for bactericidal activity.

Example 5

Bactericidal Activity of Isolated Domain II and III Peptides

Figure 9A:
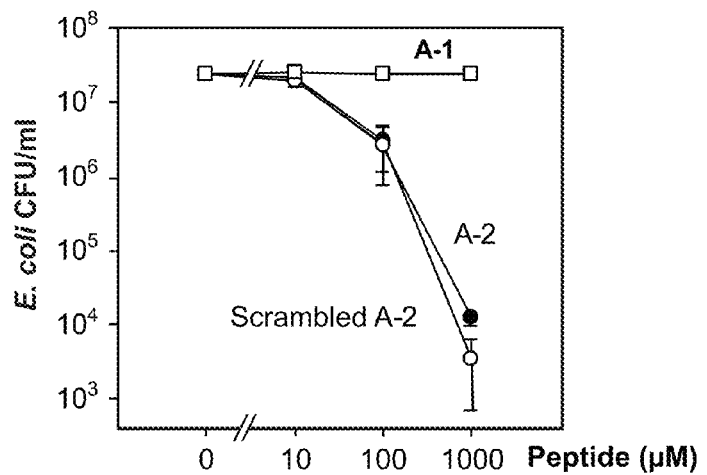
FIGS. 9 A & B are graphs showing the bactericidal activity of domain II and domain III free peptides. *E. coli* were subjected to the bactericidal assay with the indicated concentrations of the peptides corresponding to the domain II in panel (A), and domain III in panel (B). Sequences of chicken leukocyte RNase A-1 are indicated with open squares and A-2 with closed circles. Also included was a peptide corresponding to domain II leukocyte RNase A-2 with the amino acid sequence scrambled (panel A, open circles), sequence as shown.

Next, synthetic peptides minimally encoding domains II and III were used to determine whether the primary structure of these domains was sufficient for bactericidal activity using. A scrambled peptide including the amino acids of RNase A-2 domain II in random order was also tested in order to assess whether the amino acid sequence itself, or rather composition, defined the activity. FIG. 9 documents the bactericidal activity of synthetic peptides. The RNase A-2 domain II peptide (pI=12.8) reduced colony count of *E. coli* in a dose-dependent manner, whereas the A-1 domain II peptide (pI=6.1) was inactive up to 1000 µM. $LD_{99}$ of A-2 domain II peptide was calculated as 200 µM. The scrambled domain II peptide reduced the colony count of *E. coli* to the same degree as the wild type A-2 domain II peptide, suggesting that amino acid composition, rather than sequence, defined the bactericidal activity. The A-2 domain III peptide (pI=12.3) was also active, and reduced colony count of *E. coli* at an even lower concentration ($LD_{99}$ for *E. coli* was 10 µM) than the A-2 domain II peptide. The A-1 domain III (pI=9.9) peptide showed no significant activity.

Figure 9B:
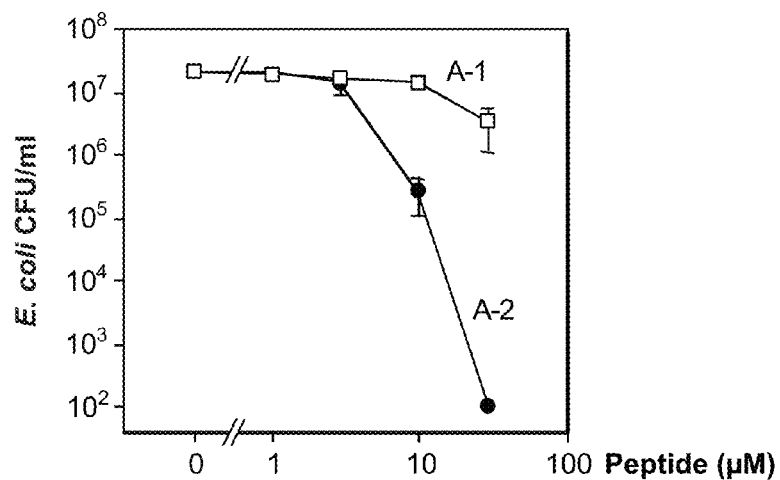
Figure 10B:
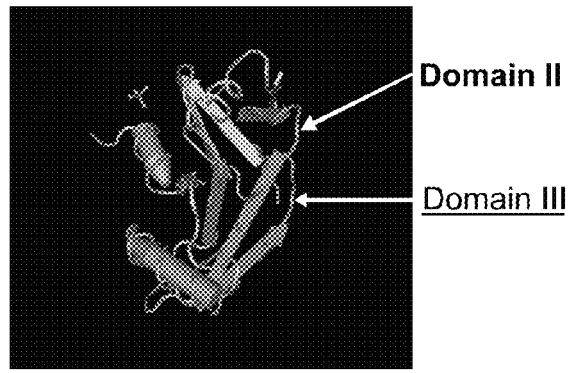
FIGS. 10 A-C are panels showing amino acid alignment and three-dimensional localization of the domain II and the domain III sequences. Panel (A) shows amino acid sequence alignments, including human angiogenin, mouse angiogenin and two chicken leukocyte RNases, with corresponding amino acid sequence for domain II (bold) and domain III (underlined) as shown. Panel (B) and (C) shows localization of domains II and III based on the amino acid sequence alignment shown in (A). Sequences corresponding to domain II are indicated with an arrowhead. Sequences corresponding to domain III are indicated with an oval head.
Figure 10C:
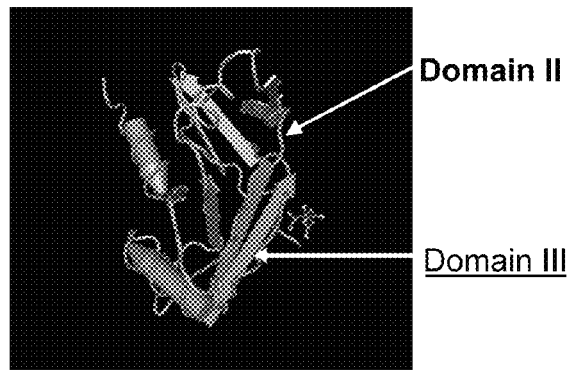

Although both A-2 domain sequences were active bactericidal agents when delivered as free peptides, the domain II peptide was more effective when delivered within the three-dimensional structure of the RNase A backbone. The A-2 domain III peptide was equally bactericidal whether delivered as a free peptide or inserted into the sequence of RNase A-1, as shown in FIG. 9B and FIG. 8B, respectively.

Taken together, these data indicate that the RNase backbone is not absolutely essential to the bactericidal mechanism, and that the A-2 domain sequences described herein are active bactericidal agents when delivered as free peptides.

Example 6

Bactericidal Activity of Isolated Domain III Peptides on a Natural Pathogen

Figure 11:
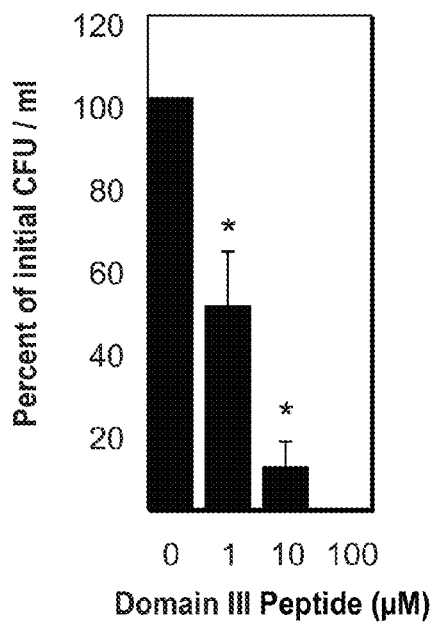
FIG. 11 is a graph showing that the domain III peptide is bactericidal for *S. enterica* serovar *pullorum* which is a natural pathogen of domestic poultry. At the highest concentration tested, 100 micromolar, RNase A-2 domain III reduces the colony count from 100-1000 fold (2-3 logs).

The bactericidal actions of the A-2 domain sequences on natural pathogens was explored. The bactericidal activity of the leukocyte RNase A-2 domain III peptide on the natural pathogen *Salmonella enterica* serovar *pullorum* was determined using the bactericidal assays as previously described. *S. enterica* is a gram negative pathogen isolated initially from domestic poultry and is as such a natural target pathogen for a bactericidal agent isolated from chicken granulocytes. As shown in FIG. 11, the domain III peptide is bactericidal for this pathogen. At the highest concentration tested, 100 micromolar, RNase A-2 domain III reduces the colony count from 100-1000 fold (2-3 logs). Thus, the A-2 domain sequences are useful bactericidal agents against natural pathogens.

Methods of the Invention

The results reported herein were obtained using the following Materials and Methods:

Isolation of Leukocytes from Bone Marrow

Bone marrow cells were collected from femurs and tibiae of White Leghorn chickens (*Gallus gallus*) by flushing sterile phosphate-buffered saline (PBS, pH 7.4) through opened bones. Cells were washed twice with PBS, and red blood cells were lysed by incubation with ACK lysing buffer (Cambrex Bio Science, Walkersville, Md.) for 5 minutes. The cells were subsequently washed again with PBS and counted with a hemocytometer. Viability was assessed by Trypan blue staining.

Isolation of Leukocytes from Peripheral Blood

Leukocytes were separated from peripheral blood according to the methods described previously [26, 27] with minor modifications. Heparinized peripheral blood was collected by cardiac puncture and then mixed with a 3% dextran solution. Red blood cells were sedimented, and the leukocyte-rich supernatant (buffy coat) was collected by centrifugation at 400×g, washed with twice with PBS and separated into phases via Lymphocyte Separation Medium (density; 1.077-1.080 g/ml at 20° C., Mediatech, Herndon, Va.) at 400×g for 30 mM at room temperature. Cells sedimenting at the base of the tube were collected as the granulocyte fraction. Red blood cells were eliminated by ACK lysing buffer, and cell number and viability were evaluated as described above.

Preparation of Cell Lysates

Isolated bone marrow cells or peripheral blood leukocytes (2×10$^6$ cells/100 µL) were mixed with PBS containing 1% Triton X-100 and 1 mM phenylmethyl-sulfonylfluoride (PMSF, Sigma-Aldrich, St. Louis, Mo.), and left on ice for 30 min. After centrifugation at 16000×g for 10 mM at 4° C., the resulting supernatant was collected and stored at −80° C. prior to use.

Preparation of RNA from Bone Marrow Cells

One mL RNAzol B (Teltest, Friendswood, Tex.), was added to each aliquot of 2×10$^6$ cells (15-25×10$^6$ cells total). Chloroform was added (1:10 (v/v)), and the samples were mixed thoroughly and incubated on ice for 15 mM. After a centrifugation at 13,600×g for 20 mM at 4° C., the aqueous layer was transferred to fresh tubes. Equal volumes of ice-cold isopropanol were added, and RNA was precipitated at −20° C., harvested by centrifugation, washed twice in 80% ethanol, dried, and resuspended in diethyl pyrocarbonate-treated water. RNA was quantitated spectrophotometrically.

Rapid Amplification of cDNA Ends (5' and 3' Race)

Complementary DNA (cDNA) was synthesized from 1 µg RNA from *Gallus gallus* bone marrow RNA with MMLV reverse transcriptase as per the manufacturer's instructions (SMART RACE cDNA Amplification kit, Clontech, Palo Alto, Calif.) and then amplified using specific oligonucleotides for chicken leukocyte RNase A-1 (previously identified as Angiogenin/RNase [20]) and chicken leukocyte RNase A-2 (previously identified as RSFR [21]).

Sequences used were as follows:

```
5' RACE for leukocyte RNase A-1,
5'-TGGAGAGGTGCCATCCAGATGCACAGGAAGCCCTCCCCG-3'
(SEQ ID NO: 28)

5' RACE for leukocyte RNase A-2,
5'-TGAATGCAACCATCTCAGGAGGGTTGAAGT-3'
(SEQ ID NO: 29)

3' RACE, 5'-GTTCCAACCTACCAAGATTTTTG-3
(SEQ ID NO: 30)
```

The PCR conditions were as follows: 5 cycles of 94° C. for 30 s followed by 72° C. for 3 min; then 5 cycles of 94° C. for 30 s followed by 70° C. for 30 s followed by 72° C. for 3 min; and finally 25 cycles of 94° C. for 30 s followed by 68° C. for 30 s followed by 72° C. for 3 min. The amplified PCR fragments were gel purified (BIO 101, Alta Vista, Calif.) and subcloned into the pCR2.1 (Invitrogen, San Diego, Calif.); multiple colonies were sequenced in both directions. The sequences were assembled using Sequencher 4.1 (GeneCodes, Ann Arbor, Mich.) to obtain the full-length cDNA sequence. To amplify the two chicken leukocyte RNases (minus signal sequences), the following primers were used: 5'-aagcttctGTTCCAACCTACCAAGATTTTTG-3' (SEQ ID NO: 31) and 5'-gaattcTGGAAAGGTGCCATCCA-GATGCAC-3' (SEQ ID NO: 32) for leukocyte RNase A-1 and 5'-aagcttctGTTCCAACCTACCAAGATTTTTG-3' (SEQ ID NO: 31) and 5'-gaattcTGGAGAGGTGCCATCCA-GATGCACAGGAAGCCCTCCCCG-3' (SEQ ID NO: 34) for leukocyte RNase A-2 (lower case letters indicate restriction sites added to facilitate subcloning). PCR with Pfx DNA polymerase was performed under the following conditions: an initial denaturation step of 94° C. for 2 min followed by 35 cycles of 94° C. for 30 sec, 55° C. for 30 sec, and 68° C. for 1 min. PCR product was subcloned into pCR-Blunt vectors (Invitrogen) as described above. Sequence analysis Automated DNA sequencing was performed using an ABI PRISM 377 DNA sequencer (Applied Biosystems, Foster City, Calif.) and a DYEnamic ET Terminator Cycle Sequencing Kit (Amersham Biosciences, Piscataway, N.J.). Sequence analyses were performed with the assistance of Sequencher 4.1 (Ann Arbor, Mich.).

Production of Recombinant Chicken Leukocyte RNases A-1 and A-2

Recombinant chicken RNase proteins were prepared in *Escherichia coli* BL21 strain using the pFLAG-CTS expression vector (Sigma-Aldrich, St. Louis, Mo.) which utilizes an IPTG-inducible promoter, an amino-terminal bacterial OmpA secretion piece, and a carboxy-terminal FLAG tag. This expression system has been used extensively for expression of recombinant RNase A ribonucleases [28-32]. Quantity of protein was determined by densitometric analysis as described previously [29].

Site-Directed Mutagenesis

Chicken ribonucleases with exchanged domains were prepared by site-directed mutagenesis using a QuikChange Site Directed Mutagenesis Kit (Stratagene, La Jolla, Calif.) according to the manufacturer's protocol. Primers used to effect site-specific mutations are shown in Table 3, below. Mutations were verified by DNA sequencing. The domains listed in Table 3 are as indicated in FIG. 6. Recombinant proteins with specific mutations were prepared as described above.

TABLE 3

Primers used for site-directed mutagenesis.

| Description | Sequences (5' -> 3') |
|---|---|
| Domain I  A1 -> A2 | ACCAAGATTTTTTGTACAAGCATATGGAC TTCCCGAAGAC (SEQ ID NO: 35) |
| | GTCTTCGGGAAGTCCATATGCTTGTACAA AAAATCTTGGT (SEQ ID NO: 36) |
| Domain I  A2 -> A1 | ACCAAGATTTTTTGCGGACGCACGTGGAC TTCCCGAAGAC (SEQ ID NO: 37) |
| | GTCTTCGGGAAGTCCACGTGCGTCCGCAA AAAATCTTGGT (SEQ ID NO: 38) |
| Domain II  A1 -> A2 | GCCCTTCGTACAACGCGGCGGCACTTTCG TATCACAGACTGTAAG (SEQ ID NO: 39) |
| | CTTACAGTCTGTGATACGAAAGTGCCGCC GCGTTGTACGAAGGGC (SEQ ID NO: 40) |
| Domain II  A2 -> A1 | GCCCTTCGTACAACGCAGCAGCAACTTCC TGTCACAGACTGTAAG (SEQ ID NO: 41) |
| | CTTACAGTCTGTGACAGGAAGTTGCTGCT GCGTTGTACGAAGGGC (SEQ ID NO: 42) |
| Domain III  A1 -> A2 | AGGAGCCATCCAACCTGCAGATACAGCGG CAATCAATTCAA (SEQ ID NO: 43) |
| | CAATCAATTCAACCGCCGGGTCCGAGTGG GGTGTCGGGGAGGGCTTCC (SEQ ID NO: 44) |
| | TTGAATTGATTGCCGCTGTATCTGCAGGT TGGATGGCTCCT (SEQ ID NO: 45) |
| | GGAAGCCCTCCCCGACACCCCACTCGGAC CCGGCGGTTGAATTGATTG (SEQ ID NO: 46) |
| Domain III  A2 -> A1 | AGGAGCCATCCAACCTGCAGTTACACCGG CAATCAATTCAA (SEQ ID NO: 47) |
| | CAATCAATTCAACCATCGGGTCCGAGTGG GGTGTTGGGGAGGGCTTCC (SEQ ID NO: 48) |
| | TTGAATTGATTGCCGGTGTAACTGCAGGT TGGATGGCTCCT (SEQ ID NO: 49) |
| | GGAAGCCCTCCCCAACACCCCACTCGGAC CCGATGGTTGAATTGATTG (SEQ ID NO: 50) |
| H110A | GGAGGGCTTCCCGTGGCTCTGGATGGCACC (SEQ ID NO: 51) |
| | GGTGCCATCCAGAGCCACGGGAAGCCCTCC (SEQ ID NO: 52) |

*The domains are as indicated in FIG. 6.

Preparation of Peptides and Anti Peptide Antisera

Peptides and anti-peptide antisera were prepared at Zymed Laboratories/Invitrogen (South San Francisco, Calif.). Purity of peptides was confirmed as >95% by mass spectrometry. Antibodies to *Gallus gallus* leukocyte RNases A-1 and A-2 were prepared by immunization of rabbits with 10 mg of KLH-conjugated sequence-specific peptides: A-1, $H_2N$-QP-NRALRTTQQQLP-COOH (SEQ ID NO: 9) and A-2, $H_2N$-DQALRTTRRHFRIT-COOH (SEQ ID NO: 10) (Zymed Laboratories/Invitrogen).

Immunoblotting

Bone marrow lysates and peripheral granulocyte lysates from *Gallus gallus* and recombinant FLAG-tagged chicken RNases were mixed with a reducing Tris-Glycine 2×SDS sample buffer (Invitrogen) and subjected to SDS-polyacrylamide gel electrophoresis (14% acrylamide, 1× Tris-glycine system). After proteins in gel were transferred onto a nitrocellulose membrane (Invitrogen), non-specific binding to the membrane was blocked with 5% non-fat dry milk in Tris-buffered saline (TBS, pH 7.5) prior to probing the membrane with a 1:200 dilution of rabbit anti-leukocyte RNase A-1, 1:200 rabbit anti-leukocyte RNase A-2, or 1:200 mouse anti-Flag M2 antibody (Sigma-Aldrich), followed by alkaline phosphatase-conjugated goat anti-rabbit IgG or anti-mouse IgG (Bio-Rad, Hercules, Calif.). The membranes were developed with AP Conjugate Substrate kit (Bio-Rad) according to the manufacturer's instructions.

Immunostaining of *Gallus gallus* Leukocytes and Observation Under Confocal Microscopy One million cells were isolated as described and washed with 3 ml 1% BSA in PBS (BSA/PBS) and then fixed and permeabilized by FIX & PERM (Caltag Laboratories, Burlingame, Calif.) as per manufacturer's protocol. Primary antibody was used at 1:100 and consisted of anti-leukocyte RNase A-1 or anti-leukocyte RNase A-2. Pre-immune serum was used as a control for background staining. After an overnight incubation in primary antibody at 4° C., the cells were washed in BSA/PBS and a FITC-conjugated secondary antibody, goat anti-rabbit IgG-FITC (BD Biosciences), was applied at a 1:100 dilution. After 1-hour incubation in the dark at room temperature, the cells were washed and the nuclear stain, 4', 6-diamidino-2-phenylindole dihydro-chloride (DAPI, Molecular probes, Eugene, Oreg.) was added at 1 μg/mL and incubated for 15 minutes in the dark. The cells were washed 2 times in BSA/PBS and then fixed onto glass slide using cytofunnels (Thermo Electron Corporation, Waltham, Mass.). Coverslips were attached after the addition of the ProLong antifade reagent (Invitrogen). Slides were stored in dark at 4° C. until imaging. Images were collected on a TCS-SP2 AOBS confocal microscope (Leica Microsystems, Mannheim, Germany) using a 63× oil immersion objective NA 1.32 at different zoom factors. The confocal pinhole was set to 0.9 Airy units to ensure maximum resolution. FITC was excited using an Argon laser at 488 nm, and DAPI, nuclear stain, was excited using an Argon laser (Enterprise model 651, Coherent, Inc., Santa Clara, Calif.) at 364 nm. Differential interference contrast images were collected simultaneously with the fluorescence images using the transmitted light detector. The settings were adjusted on a pre-immune slide for each cell type and were not changed for images collected with relevant primary antibody.

Ribonuclease Assays

The ribonuclease (RNase) assay with yeast tRNA substrate has been described in detail elsewhere [29]. In this study, 10 μL of a 20 mg/ml solution of yeast tRNA, polyuridylic acid (poly U), polyadenylic acid (poly A), polycytidylic acid (poly C), polyguanylic acid (poly G), or polyinosinic acid (poly I)

(Sigma-Aldrich) were added to 800 µl of 40 mM sodium phosphate buffer, pH 7.0 containing recombinant FLAG-tagged chicken RNase protein. In experiments in which the pH optimum was to be determined, 40 mM sodium phosphate buffers of pH 5.0, 5.5, 6.0, 6.5, 7.4 or 8.0 were used instead of the buffer of pH 7.0. In some experiments, 200 U human placental RNase inhibitor (Boehringer Mannheim) were added prior to the addition of the tRNA substrate. Conversion of units $A_{260}$ per unit time to pmol/s were performed as described in [29], based on the following conversion factors: the average molecular weight of a molecule of tRNA is 28,100 (75-90 ribonucleotides/tRNA molecule×341 MW per ribonucleotide) with an $A_{260}$ of 1.0 corresponding to 40 µg of RNA.

Angiogenesis Assay

The chick aortic ring sprouting assay was performed as described previously [33] with minor modifications. Aortic arches were dissected from 13-day-old chicken embryos, cleaned free of unwanted tissue and cut into 0.8 mm slices. Each ring was transferred into center of a well of 96-well plate. Ice-cold 10 µl of Matrigel (Becton Dickinson, Bedford, Mass.) were added immediately to imbed the ring. After the Matrigel was solidified, 100 µl of human endothelial-SFM basal growth medium (Invitrogen) was added to each well. After addition of recombinant leukocyte RNase A-1 or RNase A-2 or control preparation, the rings were incubated at 37° C. for 24 h. Vessels sprouted from rings were observed under microscopy, and assessed by blinded observers. Each groups composed of 6 to 8 rings.

Bactericidal Assays

Bactericidal assays were performed as described previously with modifications [28]. Briefly, 100 microliters from a single bacterial colony overnight culture grown in Luria-Bertani (LB) broth was diluted 1:100 in 100 mM sodium phosphate, pH 7.4, collected by centrifugation, and resuspended in 1 ml sodium phosphate, pH 7.4. Ten microliters of bacteria in buffer are incubated for 4 hr at 37° C. with 10 microliters recombinant protein or peptide at concentrations indicated, or diluent control and were then diluted 10, 100, or 1000-fold prior to plating on LB agar for overnight growth for colony counts. All points were determined in triplicate.

Phylogenetic Analysis

Sequence data was analyzed using algorithms included in the MEGA program [34] that is available for downloading online. Sequences were aligned using ClustalW for import into MEGA. All sequence data is available online at GenBank or NCBI databases. Accession numbers for sequences used in statistical analyses include: *Gallus gallus* leukocyte RNase A-1 (RNase/angiogenin), DQ395275; *Gallus gallus* leukocyte RNase A-2 (RSFR), DQ395276; *Gallus gallus* liver RNase (RNase CL2), DQ395277, P81476; *Iguana iguana* RNase, AY780490; *Chelydra serpentina* RNase, PO4061; *Rana pipiens* onconase, AAL54383; *Rana japonica* RNase, P18839; *Rana catesbeiana* RC203, AAK30253; *Homo sapiens* pancreatic RNase 1, NP_002924; *Homo sapiens* EDN/RNase 2, NP_002925; *Homo sapiens* ECP/RNase 3, NP_002926; *Homo sapiens* RNase 4, P34096; *Homo sapiens* angiogenin/RNase 5, NP_001136; NP_002924; *Homo sapiens* RNase k6, AAH20848; *Homo sapiens* RNase 7, AY170392; *Homo sapiens* RNase 8, AF473854; *Mus musculus* pancreatic RNase 1, NP_035401; *Mus musculus* Ear 1, P97426; *Mus musculus* Ear 2, P97425; *Mus musculus* Ear 6, AAP82022; *Mus musculus* Ear 11, AAH20070; *Mus musculus* RNase 4, NP_067447; *Mus musculus* angiogenin-1/RNase 5, NP_031473; *Mus musculus* angiogenin-2, NP_031475; *Mus musculus* angiogenin-3, NP_031474; *Mus musculus* angiogenin-4, AY219870; *Mus musculus* angiogenin-6, AY665821; *Mus musculus* RNase 6, NP_084374.

Statistical Analysis

Data are shown as the mean±SEM for the numbers of samples. The student's t-test was performed for statistical analysis of the differences between the groups.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

CITATIONS

The following documents are cited herein. Many of the following documents are referred to above by a reference number as listed sequentially below within brackets, e.g.

1. Matousek, J. (2001) Comp Biochem Physiol C Toxicol Pharmacol., 129, 175-191.
2. Strydom D J. (1998) Cell Mol Life Sci. 54, 811-824.
3. Spalletti-Cernia, D., Sorrentino, R., Di Gaetano, S., Arciello, A., Garbi, C., Piccoli, R., D'Alessio, G., Vecchio, G., Laccetti, P., Santoro, M. (2003) J Clin Endocrinol Metab. 88, 2900-2907.
4. Yang, D., Rosenberg, H. F., Chen, Q., Dyer, K. D., Kurosaka, K., and Oppenheim, J. J. (2003) Blood 102, 3396-3403.
5. Dyer, K. D., and Rosenberg, H. F. (2006) Molecular Diversity. In press.
6. Beinterna, J. J., and Kleineidam, R. G. (1998) Cell. Mol. Life. Sci. 54, 825-32.
7. Leland, P. A., and Raines, R. T. (2001) Chem. Biol. 8, 405-413.
8. Rosenberg, H. F. and Domachowske, J. B. (2001) J Leukoc Biol. 70, 691-698.
9 Penttinen, J., Pujianto, D. A., Sipila, P., Huhtaniemi, I., Poutanen, M. (2003) Mol Endocrinol 17, 2138-2151.
10. Castella, S. et al., (2004) Biol. Reprod. 70, 319-328.
11. Cho, S., Beinterna J. J., and Zhang, J. (2005) Genomics 85, 208-220.
12. Castella, S., Benedetti, H., de Llorens, R., Dacheux J. L., and Dacheux, F. (2004) Biol. Reprod. 71, 1677-1687.
13. Devor, E. J., Moffat-Wilson, K. A., and Galbraith, J. J. (2004) Hum. Biol. 76, 921-935
14. Cho, S, and Zhang, J. (2006) Gene 373, 116-125
15. Irie, M., Nitta, K., and Nonaka, T. (1998) Cell Mol Life Sci. 54, 775-784.
16. Liao, Y. D., Huang, H. C., Leu, Y. J., Wei, C. W., Tang, P. C., Wang, S. C. (2000) Nucleic Acids Res. 28, 4097-4104.
17. Lou, Y. C., Huang, Y. C., Pan, Y. R., Chen, C., and Liao, Y. D. (2005) J Mol. Biol. 355, 409-421.
18. Rosenberg, H. F., Zhang, J., Liao, Y. D., and Dyer, K. D. (2001) J. Mol. Evol. 53, 31-38.

19. Costanzi J., Sidransky, D., Navon, A., and Goldsweig, H. (2005) Cancer Invest. 23, 643-650
20. Nakano, T., and Graf, T. (1992) Oncogene 7, 527-534
21. Klenova, E. M., Botezato, I., Laudet, V., Goodwin, G. H., Wallace, J. C., and Lobanenkov, V. V. (1992) Biochem. Biophys. Res. Commun. 185, 231-239
22. Hayano, K., Iwama, M., Sakamoto, H., Watanabe, H., Sanda, A., Ohgi, K., and Irie, M. (1993) J. Biochem. (Tokyo) 114, 156-162
23. Zhao, W., Beinterna, J. J., and Hofsteenge, J. (1994) Eur. J. Biochem. 219, 641-646
24. Nitto, T., Lin, C., Dyer, K. D., Wagner, R. A., and Rosenberg, H. F. (2005) Gene 352, 36-44.
25. Beinterna, J. J., Broos, J., Meulenberg, J., and Schuller, C. (1985) Eur. J. Biochem. 153, 305-312.
26. Rath, N. C., Huff, G. R., Balog, J. M., and Huff, W. E. (1998) Vet. Immunol. Immunopathol. 64, 83-95
27. Seo, S. H., Pei, J., Briles, W. E., Dzielawa, J., and Collisson, E. W. (2000) Virology 269, 183-189
28. Rosenberg, H. F. (1995) J Biol. Chem. 270, 7876-7881.
29. Rosenberg, H. F., and Dyer, K. D. (1995) J Biol. Chem. 270, 21539-21544.
30. Nitto, T., Dyer, K. D., Mejia, R. A., Bystrom, J., Wynn, T. A., and Rosenberg, H. F. (2004) Genes Immun. 5, 668-674.
31. Dyer, K. D., Rosenberg, H. F., and Zhang, J. (2004) J Mol. Evol. 59, 657-665.
32. Rosenberg, H. F., and Dyer, K. D. (1997) Nucleic Acids Res. 25, 3532-3536.
33. Clement, P. M., Hanauske-Abel, H. M., Wolff, E. C., Kleinman, H. K., and Park, M. H. (2002) Int: J. Cancer. 100, 491-498
34. Kumar, S., Tamura, K., Jakobsen, I. B., and Nei, M. (2001) Bioinformatics 17, 1244-1245
35. Harder, J., and Schroder, J. M. (2002) J Biol. Chem. 277, 46779-46784.
36. Zhang, J., Dyer, K. D., and Rosenberg, H. F. (2003) Nucleic Acids Res. 31, 602-607.
37. Hooper, L. V., Stappenbeck, T. S., Hong, C. V., and Gordon, J. I. (2003). Nat. Immunol. 4, 269-273.
38. Schermer, S. (1967) The blood morphology of laboratory animals. 3rd ed. Philadelphia: F.A. Davis Co.
39. Swaggerty, C. L., Ferro, P. J., Pevzner, I. Y., and Kogut, M. H. (2005) FEMS Immunol. Med. Microbiol. 43, 149-154.
40. Bojesen, A. M., Petersen, K. D., Nielsen, O. L., Christensen, J. P., and Bisgaard, M. (2004) Avian Dis. 2004 48, 463-470.
41. Mellata, M., Dho-Moulin, M., Dozois, C. M., Curtiss, R. 3rd, Lehoux, B., Fairbrother, J. M. (2003) Infect. Immun. 71, 494-503.
42. Farnell, M. B., He, H., Genovese, K., and Kogut, M. H. (2003) Int. Immunopharmacol. 3, 1677-1684
43. Evans, E. W., Beach, G. G., Wunderlich, J., and Harmon, B. G. (1994) J. Leukoc. Biol. 56, 661-665.
44. Kogut, M. H., Rothwell, L., and Kaiser, P. (2003) J. Interferon Cytokine Res. 23, 319-327.
45. Swaggerty, C. L., Kogut, M. H., Ferro, P. J., Rothwell, L., Pevzner, I. Y., and Kaiser, P. (2004) Immunology 113, 139-148.
46. Zijlstra, A., Seandel, M., Kupriyanova, T. A., Partridge, J. J., Madsen, M. A., Hahn-Dantona, E. A., Quigley, J. P., and Deryugina, E. I. (2006) Blood 107, 317-327.
47. Iyer, S., Holloway, D. E., Kumar, K., Shapiro, R., and Acharya, K. R. (2005) J. Mol. Biol. 347, 637-655.
48. Papageorgiou, A. C., Shapiro, R., and Acharya, K. R. (1997) EMBO J. 16, 5162-5177.
49. Dickson, K. A., Haigis, M. C., and Raines, R. T. (2005) Prog Nucleic Acid Res Mol. Biol. 80, 349-374.
50. Wu, Y., Mikulski, S. M., Ardelt, W., Rybak, S. M., and Youle, R. J. (1993) J. Biol. Chem. 268, 10686-10693
51. Dijkstra, J., Touw, J., Halsema, I., Gruber, M., Ab, G. (1978) Biochim Biophys Acta. 521, 363-373
52. Caldwell, R. B., Kierzek, A. M., Arakawa, H., Bezzubov, Y., Zaim, J., Fiedler, P., Kutter, S., Blagodatski, A., Kostovska, D., Koter, M., Plachy, J., Carninci, P., Hayashizaki, Y. and Buerstedde, J. M. (2005) Genome Biol. 6, R6.
53. Rosenberg, H. F., Dyer, K. D., Tiffany, H. L., and Gonzalez, M. (1995) Nat. Genet. 10, 219-223
54. Zhang, J., Rosenberg, H. F., and Nei, M. (1998) Proc Natl Acad Sci USA. 95, 3708-3713.
55. Singhania, N. A., Dyer, K. D., Zhang, J., Deming, M. S., Bonville, C. A., Domachowske, J. B., and Rosenberg, H. F. (1999). J Mol. Evol. 49, 721-728.
56. Zhang, J., Dyer, K. D., and Rosenberg, H. F. (2000) Proc Natl Acad Sci USA, 97, 4701-4716.
57. Auerbach R, Lewis R, Shinner Bin Kubai L and Akhtar N. (2003) Clinical Chemistry.

What is claimed is:

1. An isolated polypeptide consisting of a sequence selected from the group consisting of:
   a) the amino acid sequence RYSGNQFNRRVRVGCRG (SEQ ID NO: 8); and
   b) the amino acid sequence TTRRHFRIT (SEQ ID NO: 6).

2. A synthetic polypeptide consisting of a sequence selected from the group consisting of:
   (i) the amino acid sequence TTRRHFRIT (SEQ ID NO: 6); and
   (ii) the amino acid sequence RYSGNQFNRRVRVGCRG (SEQ ID NO: 8).

3. A pharmaceutical composition comprising a polypeptide according to claim 2 and a pharmaceutically acceptable carrier.

4. A method for inhibiting the growth of *Salmonella enterica* serovar *pulloram* bacteria in vitro, the method comprising:
   a) contacting *Salmonella enterica* serovar *pulloram* bacteria in vitro with a synthetic polypeptide of claim 2 at a concentration of 100 micromolar, wherein the synthetic polypeptide of claim 2 is SEQ ID NO: 8; and
   b) measuring the growth of said *Salmonella enterica* serovar *pulloram* bacteria in vitro, wherein a reduction in colony count of said *Salmonella enterica* serovar *pulloram* bacteria of 100 to 1000 fold as compared to an appropriate control indicates inhibition of *Salmonella enterica* serovar *pulloram* bacteria by said synthetic polypeptide,
   thereby inhibiting the growth of said *Salmonella enterica* serovar *pulloram* bacteria in vitro.

* * * * *